(12) United States Patent
McNair

(10) Patent No.: US 11,278,246 B1
(45) Date of Patent: Mar. 22, 2022

(54) DETERMINING RESPIRATORY DETERIORATION AND DECISION SUPPORT TOOL

(71) Applicant: CERNER INNOVATION, INC., Kansas City, KS (US)

(72) Inventor: Douglas S. McNair, Leawood, KS (US)

(73) Assignee: CERNER INNOVATION, INC., North Kansas City, MO (US)

( * ) Notice: Subject to any disclaimer, the term of this patent is extended or adjusted under 35 U.S.C. 154(b) by 684 days.

(21) Appl. No.: 16/125,467

(22) Filed: Sep. 7, 2018

Related U.S. Application Data

(60) Provisional application No. 62/555,618, filed on Sep. 7, 2017.

(51) Int. Cl.
| | | |
|---|---|---|
| *A61B 5/00* | (2006.01) | |
| *A61B 5/08* | (2006.01) | |
| *A61B 7/04* | (2006.01) | |
| *A61B 7/00* | (2006.01) | |

(52) U.S. Cl.
CPC .......... *A61B 5/7275* (2013.01); *A61B 5/0803* (2013.01); *A61B 5/0816* (2013.01); *A61B 5/7203* (2013.01); *A61B 5/726* (2013.01); *A61B 5/7239* (2013.01); *A61B 5/7257* (2013.01); *A61B 5/7282* (2013.01); *A61B 5/746* (2013.01); *A61B 7/003* (2013.01); *A61B 7/04* (2013.01)

(58) Field of Classification Search
CPC ... A61B 5/7275; A61B 5/0803; A61B 5/0816; A61B 5/7203; A61B 5/7239; A61B 5/7257; A61B 5/726; A61B 5/7282; A61B 5/746; A61B 7/003; A61B 7/04
See application file for complete search history.

*Primary Examiner* — Christian Jang
*Assistant Examiner* — Mitchell E Alter
(74) *Attorney, Agent, or Firm* — Shook, Hardy & Bacon L.L.P.

(57) ABSTRACT

Decision support technology is provided for use with patients who may experience respiratory deterioration. A mechanism is provided to determine an indicator of a patient's probability of deterioration of respiratory functioning, which may include calculating a probability of a respiratory deterioration event in patients from whom serial digital recordings of respiratory sounds are acquired. A forecast or score representing a likelihood of deterioration may be generated and used for pulmonary disease prognosis, diagnosis, and/or determining or implementing an appropriate response action such as automatically issuing an alert or notification to a caregiver associated with the patient.

20 Claims, 18 Drawing Sheets

```
###########################################################

#   Adaptive multitaper power spectrum analysis of digital stethoscope waveforms

##################################################### library(psd)
library(tuneR)
library(signal)

# load pneumophonography digital audio
mp1 <- readMP3(file="c:/0_cerdsm/IP/copd_telestethoscope/MP3/n_normal_vesicular01.mp3")
mp2 <- readMP3(file="c:/0_cerdsm/IP/copd_telestethoscope/MP3/p_insp_crackles_pneumonia.mp3")

# trim silent leader or trailer
bound1 <- which(mp1@left > 0)
lb1 <- min(bound1)
ub1 <- max(bound1)
ts1 <- mp1@left[lb1:ub1]

bound2 <- which(mp2@left > 0)
lb2 <- min(bound2)
ub2 <- max(bound2)
ts2 <- mp2@left[lb2:ub2]

# pre-whiten the timeseries; typ 40 sec on 2.7GHz single-core with 15-sec 44.1KHz 16-bit data
ts1 <- prewhiten(ts1, AR.max=10, zero.pad="rear")
ts2 <- prewhiten(ts2, AR.max=10, zero.pad="rear")

# determine multi-taper power spectrum; typ. 90 sec on 2.7GHz single-core with 15-sec 44.1KHz 16-bit data
psd1 <- pspectrum(ts1$prew_lm[1:500000])
psd2 <- pspectrum(ts2$prew_lm[1:500000])

# plot the power spectrum
plot(psd1, log='dB', lwd=3, col="red", ylim=c(-5,100), main="")
plot(psd2, log='dB', lwd=3, col="red", ylim=c(-5,100), main="")

-------- load pneumophonography digital audio
mp1 <- readMP3(file="c:/0_cerdsm/IP/copd_telestethoscope/MP3/n_normal_vesicular02.mp3")
mp2 <- readMP3(file="c:/0_cerdsm/IP/copd_telestethoscope/MP3/p_crackles_coarse01.mp3")

# trim silent leader or trailer
bound1 <- which(mp1@left > 0)
lb1 <- min(bound1)
ub1 <- max(bound1)
ts1 <- mp1@left[lb1:ub1]

bound2 <- which(mp2@left > 0)
lb2 <- min(bound2)
ub2 <- max(bound2)
ts2 <- mp2@left[lb2:ub2]

# pre-whiten the timeseries; typ 40 sec on 2.7GHz single-core with 15-sec 44.1KHz 16-bit data
ts1 <- prewhiten(ts1, AR.max=10, zero.pad="rear")
ts2 <- prewhiten(ts2, AR.max=10, zero.pad="rear")
```

CONTINUES IN FIG. 6B

*FIG. 6A.*

CONTINUES FROM FIG. 6A

```r
# determine multi-taper power spectrum; typ. 90 sec on 2.7GHz single-core with 15-sec 44.1KHz 16-bit data
psd1 <- pspectrum(ts1$prew_lm[1:500000])
psd2 <- pspectrum(ts2$prew_lm[1:500000])

# plot the power spectrum
plot(psd1, log='dB', lwd=3, col="red", ylim=c(-5,100), main="")
plot(psd2, log='dB', lwd=3, col="red", ylim=c(-5,100), main="")

-------- load pneumophonography digital audio
mp1 <- readMP3(file="c:/0_cerdsm/IP/copd_telestethoscope/MP3/n_normal_vesicular03.mp3")
mp2 <- readMP3(file="c:/0_cerdsm/IP/copd_telestethoscope/MP3/p_rhonchi01.mp3")

# trim silent leader or trailer
bound1 <- which(mp1@left > 0)
lb1 <- min(bound1)
ub1 <- max(bound1)
ts1 <- mp1@left[lb1:ub1]

bound2 <- which(mp2@left > 0)
lb2 <- min(bound2)
ub2 <- max(bound2)
ts2 <- mp2@left[lb2:ub2]

# pre-whiten the timeseries; typ 40 sec on 2.7GHz single-core with 15-sec 44.1KHz 16-bit data
ts1 <- prewhiten(ts1, AR.max=10, zero.pad="rear")
ts2 <- prewhiten(ts2, AR.max=10, zero.pad="rear")

# determine multi-taper power spectrum; typ. 90 sec on 2.7GHz single-core with 15-sec 44.1KHz 16-bit data
psd1 <- pspectrum(ts1$prew_lm[1:500000])
psd2 <- pspectrum(ts2$prew_lm[1:500000])

# plot the power spectrum
plot(psd1, log='dB', lwd=3, col="red", ylim=c(-5,100), main="")
plot(psd2, log='dB', lwd=3, col="red", ylim=c(-5,100), main="")

-------- load pneumophonography digital audio
mp1 <- readMP3(file="c:/0_cerdsm/IP/copd_telestethoscope/MP3/n_normal_vesicular04.mp3")
mp2 <- readMP3(file="c:/0_cerdsm/IP/copd_telestethoscope/MP3/p_stridor01.mp3")

# trim silent leader or trailer
bound1 <- which(mp1@left > 0)
lb1 <- min(bound1)
ub1 <- max(bound1)
ts1 <- mp1@left[lb1:ub1]

bound2 <- which(mp2@left > 0)
lb2 <- min(bound2)
ub2 <- max(bound2)
ts2 <- mp2@left[lb2:ub2]
```

CONTINUES IN FIG. 6C

*FIG. 6B.*

CONTINUES FROM FIG. 6B

.
.

```
# pre-whiten the timeseries; typ 40 sec on 2.7GHz single-core with 15-sec 44.1KHz 16-bit data
ts1 <- prewhiten(ts1, AR.max=10, zero.pad="rear")
ts2 <- prewhiten(ts2, AR.max=10, zero.pad="rear")

# determine multi-taper power spectrum; typ. 90 sec on 2.7GHz single-core with 15-sec 44.1KHz 16-bit data
psd1 <- pspectrum(ts1$prew_lm[1:500000])
psd2 <- pspectrum(ts2$prew_lm[1:500000])

# plot the power spectrum
plot(psd1, log='dB', lwd=3, col="red", ylim=c(-5,100), main="")
plot(psd2, log='dB', lwd=3, col="red", ylim=c(-5,100), main="")

```
###########################################################

# Determine roughness of a power spectrum in band 0.1 to 0.3 dimensionless frequency
# as integral of second derivative or Hausdorff dimension of spectrum log amplitude

##################################################### library(nlme)
library(rpart)
library(spatstat)

# if std is set to TRUE then x is normalized
rough <- function (x, std=TRUE) {
   if (std)
      x <- x/max(x)
   deriv2 <- diff(x, 1, 2)
   roughness <- sum(deriv2^2, na.rm=TRUE)
   return(roughness)
} haus <- function (A, B) {
   bb <- boundingbox(as.rectangle(A), as.rectangle(B))
   A <- rebound(A, bb)
   B <- rebound(B, bb)
   dA <- distmap(A)
   dB <- distmap(B)
   Z <- eval.im(abs(dA - dB))
   h_dim <- summary(Z)$max
   return(h_dim)
} initialize window objects to contain power spectra
set.seed(1239)
X <- runifpoint(135000)
Y <- runifpoint(135000)
X$x <- (1:135000)/135000
X$y <- 1e-06*runif(135000)
Y$x <- (1:135000)/135000
Y$y <- 1e-06*runif(135000)

length(psd1$spec)
# 250000

# 0.03 to 0.30 is segment index from 15001 to 150000 inclusive on Nyquist freq scale 0.0
# to 0.5 that is 250K elts long
```

.
.
.

CONTINUES IN FIG. 7B

*FIG. 7A.*

CONTINUES FROM FIG. 7A

```
normal vesicular breathing (standard against which roughness of subsequent spectra of same
patient or other patients is compared)
rough(10*log10(psd1$spec[15001:150000]))
# [1] 1.9e-06
xmin <- min(psd1$spec[15001:150000])
xmax <- max(psd1$spec[15001:150000])
X$y <- (psd1$spec[15001:150000] - xmin)/xmax
ymin <- min(psd1$spec[15001:150000])
ymax <- max(psd1$spec[15001:150000])
Y$y <- (psd1$spec[15001:150000] - ymin)/ymax
haus(X, Y)
[1] 0.000 pneumonia slight crackles
rough(10*log10(psd2$spec[15001:150000]))
# [1] 0.0047
ymin <- min(psd2$spec[15001:150000])
ymax <- max(psd2$spec[15001:150000])
Y$y <- (psd2$spec[15001:150000] - ymin)/ymax
haus(X, Y)
[1] 0.173 crackles
rough(10*log10(psd2$spec[15001:150000]))
# [1] 0.0546
ymin <- min(psd2$spec[15001:150000])
ymax <- max(psd2$spec[15001:150000])
Y$y <- (psd2$spec[15001:150000] - ymin)/ymax
haus(X, Y)
[1] 0.234 ronchi
rough(10*log10(psd2$spec[15001:150000]))
# [1] 0.0733
ymin <- min(psd2$spec[15001:150000])
ymax <- max(psd2$spec[15001:150000])
Y$y <- (psd2$spec[15001:150000] - ymin)/ymax
haus(X, Y)
[1] 0.237 stridor
rough(10*log10(psd2$spec[15001:150000]))
# [1] 0.0994
ymin <- min(psd2$spec[15001:150000])
ymax <- max(psd2$spec[15001:150000])
Y$y <- (psd2$spec[15001:150000] - ymin)/ymax
haus(X, Y)
# [1] 0.228
```

*FIG. 7B.*

```
################################################

# Bayesian method for univariate changepoint detection in power spectrum
# roughness timeseries

########################################## library(grid)
library(bcp)

# load timeseries of power spectrum roughness determination (e.g., Hausdorff dimension)
haus <- read.csv(file="c:/0_cerdsm/IP/copd_telestethoscope/haus.csv", header=TRUE,
colClasses="numeric")

# display original roughness timeseries
plot(1:60, haus$h_dim, ty='l', col='red')

# determine likely univariate changepoint(s)
set.seed(1239)
bcp.1a <- bcp(haus$h_dim, burnin=1000, mcmc=5000)

# display Bayesian posterior means and changepoint probabilities timeseries
plot(bcp.1a, main="COPD Power Spectrum Hausdorff Dimension")

# determine location of changepoint(s) (if any) whose probability exceeds 50%
which(bcp.1a$posterior.prob > 0.50)
# [1] 49
# Day-49 reflects deterioration of pulmonary function leading to ED visit on Day-50 and admission to
hospital
```

*FIG. 8.*

DETERMINING RESPIRATORY DETERIORATION AND DECISION SUPPORT TOOL

CROSS-REFERENCE TO RELATED APPLICATIONS

This application claims the benefit of U.S. Provisional Application No. 62/555,618, entitled "Determining Respiratory Deterioration and Decision Support Tool," filed Sep. 7, 2017, which is expressly incorporated by reference in its entirety.

BACKGROUND

Potentially life-threatening deterioration of respiratory status may arise in patients who have chronic respiratory conditions. Such patients often have a history of exacerbations and remissions of respiratory deterioration such as lead them to experience repeated presentations to emergency departments (EDs) or other acute care facilities. Frequently, however, there is no obvious or apparent abnormality in the oxygen saturation (SpO2) or respiratory rate or forced expiratory volume in 1 second (FEV1) or other clinical or laboratory variables that precedes the deterioration and, in such instances, ordinary threshold transgressions of the nominal limits of the reference ranges for these measurements are inadequate, frequently giving 'false-negative' assurance that there will be no near-term deterioration in the patient's status when in fact deterioration does materialize.

In other instances, fluctuations in the values of spirometric or other pulmonary function variables that may be utilized give rise to 'false-positive' alarms, incorrectly identifying a given patient as one in whom respiratory decompensation is likely when in fact no such event occurs. In such a situation, valuable resources associated with intensified monitoring or other interventions are misapplied. The resources are allocated to the given patient, in whom those resources are not in fact necessary and provide no benefit, and, insofar as resources are finite and in short supply, those resources are during that same time interval withheld from other patients, for whom the resources might have provided greater value and benefit.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Improved monitoring and decision support technology is provided for human patients who may experience respiratory deterioration. In particular, a mechanism is provided to determine an indicator of a patient's probability of deterioration of respiratory functioning, which may include calculating a probability of a respiratory deterioration event in patients from whom serial digital recordings of respiratory sounds are acquired. A forecast or score representing a likelihood of deterioration may be generated and used for pulmonary disease prognosis, diagnosis, and/or determining or implementing an appropriate response action such as automatically issuing an alert or notification to a caregiver associated with the patient.

In one embodiment, the mechanism utilizes a time series of spectral roughness determined using digitized respiration sound information from a human patient, which may be received from a recording digital stethoscope sensor. A multi-taper power spectrum may be determined from recorded respiratory cycles of the patient and used for determining spectral roughness, such as by integral of second derivative or Hausdorff Dimension. From a time series of roughness determinations corresponding to a plurality of respiratory cycles, a changepoint detection analysis is applied, and based on the changepoint(s), determining that respiratory deterioration is likely and invoking one or more actions. Further, the changepoint(s) may be determined as a probability of exceeding a change threshold and may further correspond to a score or forecast representing a likelihood that the particular patient is experiencing or will experience respiratory deterioration. Based on the generated forecast and/or score, one or more actions may be carried out automatically or may be recommended, such as, without limitation, intervening in the patient's care, modifying a care program for treating the patient, automatically scheduling interventions or consultations with specialist caregivers, or generating notifications such as electronic messages, which may include recommendations, information, alerts, or alarms, based on the forecast which may be emitted or otherwise provided to the caregiver and/or to the patient. Some embodiments may be used for continually tracking a clinical respiratory status of a patient in an ambulatory setting or at home.

In this way, embodiments disclosed herein may facilitate allowing in-home caregivers, physicians, nurses, and clinical case managers to provide more safe and effective care for each patient, especially those who have a history of exacerbations and remissions of respiratory deterioration such as lead them to experience repeated presentation to an emergency department (ED) or other acute care facility. Moreover, recognizing a high risk of deterioration far enough in advance of the onset of deterioration can guide rational allocation of resources, including intensified monitoring or treatments that may achieve reduction of risks of acute respiratory failure and/or admission to hospital or other health conditions, decreased length-of-stay in acute care institutions, financial savings, or other benefits.

BRIEF DESCRIPTION OF THE DRAWINGS

The present invention is described in detail below with reference to the attached drawing figures, wherein:

FIGS. 6A-6C illustratively provide an example embodiment of a computer program routine for generating a multi-taper power spectrum of digitized respiratory sound information, in accordance with an embodiment of the present disclosure;

FIGS. 7A-7B illustratively provide an example embodiment of a computer program routine for determining roughness of a power spectrum, such as the multi-taper power spectrum determined using the computer program routine of FIGS. 6A-6C; and FIG. 8 illustratively provides an example embodiment of a computer program routine for changepoint detection and performing a comparison of changepoint(s) against a change threshold of 0.5, in accordance with an embodiment of the present disclosure.

DETAILED DESCRIPTION

Figure 1A:
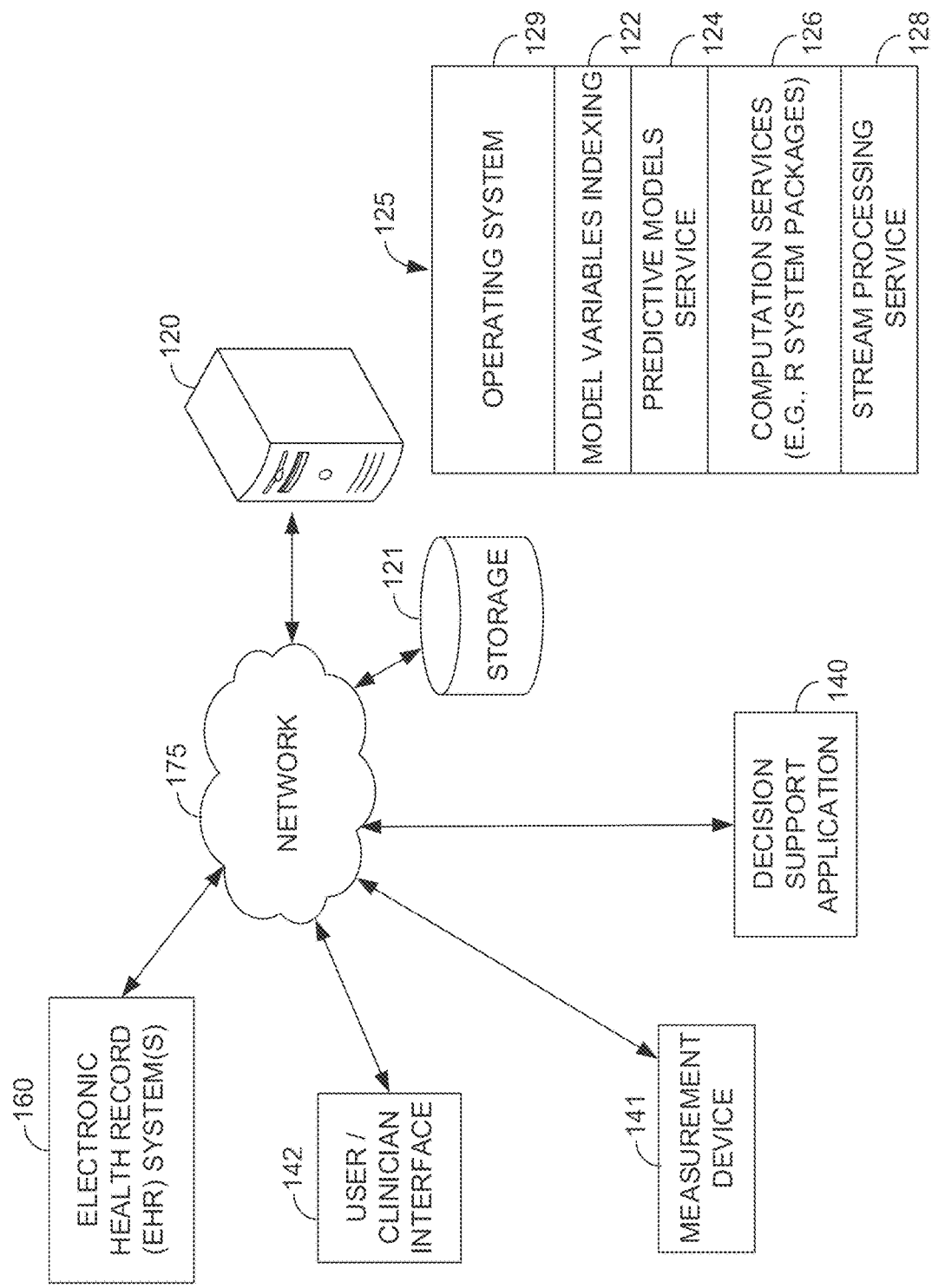
FIGS. 1A and 1B depict aspects of an illustrative architecture suitable for practicing an embodiment of the present disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other non-transitory memory technology, CD-ROM, digital versatile discs (DVD), holographic media or other optical disc storage, magnetic cassettes, magnetic tape, magnetic disk storage, other magnetic storage devices, and other computer hardware or non-transitory storage devices. These technologies can store data momentarily, temporarily, or permanently.

Aspects of the technology described herein provide improved decision support for the healthcare of patients who may experience respiratory deterioration. For instance, embodiments described herein may be utilized for monitoring patients (including patients at home or ambulatory settings or for telemedicine scenarios) and quantitatively determining whether or not a significant change in their respiratory function status meriting medical intervention has likely materialized or is in the process of emerging. In an embodiment, a clinical decision support tool is provided that determines a likelihood, which may be expressed as a score or forecast, of deterioration of respiratory function. The information utilized for determining the forecast or score may be derived from audio recordings (or similar information) of a patient's respiration, such as information received from a recording digital stethoscope sensor or similar patient monitor. The score (or forecast) may include a statistical probability or prediction, which may be used by the decision support tool to determine and/or invoke a particular action in response to the score. For example, based on the generated forecast, one or more actions may be carried out automatically or may be recommended, such as, without limitation, intervening in the patient's care, modifying a care program for treating the patient, automatically scheduling interventions or consultations with specialist caregivers, or generating notifications such as electronic messages, which may include recommendations, information, alerts, or alarms, based on the forecast which may be emitted or otherwise provided to the caregiver and/or to the patient. In some embodiments, a score or indicator or a patient's probability of deterioration may be provided and utilized to determine recommendations regarding intervention or other changes in treatments plans. Intervening actions may also include recommendations or preventive actions that may be clinically indicated and such that the patient's adherence to effective prevention or treatment regimens yields indicia of reduced risk.

More specifically, embodiments disclosed herein provide improved diagnostic and predictive decision support technology to facilitate patient care by identifying subtle patterns in respiratory sounds' spectral roughness properties that presage departures from homeostatic conditions, which can in turn lead to respiratory failure events or unplanned presentation to acute health care facilities such as emergency departments (EDs). Early detection of such spectral patterns may lead to more timely treatment, less risk of respiratory failure and reduced risk of death. Further, measurement of respiratory information, including more frequent measurements is now more easily obtainable since the introduction of inexpensive digital stethoscope devices. In some embodiments, more frequent measurements enable even earlier detection (or prediction) of likely respiratory deterioration.

For example, some embodiments described herein entail a system that can accommodate frequent acquisition and radio transmission of digital respiratory sounds recordings performed by the patient or by an in-home caregiver, to a computing device (such as a smartphone, backend server, or other computing device) that implements a method embodiment described herein, such as methods including power spectrum determination and spectral roughness estimation. Further, an advantage and improvement of these embodiments, verses conventional technologies for monitoring respiration and determining deterioration, is that embodiments described herein do not require that the serial respiratory sounds measurements be made at precise, periodic intervals but instead tolerate significant clock or phase jitter in the measured time series. Accordingly, such solutions, as provided by these embodiments, are particularly advantageous for patients from whom serial digital recordings of respiratory sounds are acquired (or acquirable or needed to be acquired) on a frequent and ongoing basis, for patients who self-record their respiratory sounds, and/or for patients in whom other scores and conventional solutions tend to yield excessive false-negative results, such as further described herein. For example, some embodiments may be particularly suitable for determining a probability of acute deterioration in a patient having a chronic respiratory condition. Some embodiments also improve on conventional decision support technologies for respiratory deterioration detection by overcoming certain drawbacks, such as providing a means for longitudinally calculating and tracking the patient's risk of acute deterioration.

Accordingly, as will be further described, systems and computerized methods are provided for monitoring the clinical and physiological status of a patient, generating a score indicating respiratory deterioration (which may be occurring or emerging, or a likelihood of deterioration of respiratory functioning, which may occur over a future time interval) and providing computer-performed decision support, which may include invoking one or more actions or recommendations. In some embodiments, these systems or methods are incorporated into a decision support tool used for screening, monitoring, and/or treating the patient.

In one aspect, a method embodiment comprises receiving (or computing) digitized respiratory sounds or information, which may be derived from audio of respiration for a particular patient, which may be obtained using a recording digital stethoscope sensor. The information may be received for a plurality of respiratory cycles of the patient. Power spectra are determined for the recorded respiratory cycles, which are then used for determining spectral roughness. For instance, roughness may be determined by integral of second derivative or Hausdorff Dimension. The roughness determinations of the plurality of respiratory cycles are assembled into a time series, based on the date-time information of the recorded respiratory event, and a changepoint detection analysis is applied to the time series. For example, in one embodiment, Bayesian methods or frequentist methods of changepoint detection may be utilized. In some embodiments, other univariate changepoint detection methods may be utilized. As further described herein, changepoint(s) may be determined as a probability of exceeding a change threshold and may further correspond to a score or forecast representing a likelihood that the particular patient is experiencing or will experience respiratory deterioration. Based on the generated forecast and/or score, one or more actions may be carried out automatically or may be recommended, as described herein. The method may be repeated as needed or if desired after a period of time, such as every 4 hours, 12 hours, daily, weekly, or the like.

Major problems in delivery of safe and effective care services in health systems involve deficiencies in the quality and continuity of patient care, including the monitoring of each patient's condition over time. Despite recent advances in electronic health records (EHR) systems, the present state of the art in medical care still does not in general utilize the accruing medical record information for active, prognostic use-cases, to predict the future status or events or outcomes that are likely to materialize for the patient. Instead, in many scenarios the EHR acts mainly as a passive repository for documenting and storing the information that is generated by each provider and each department, which characterizes the current or previous status or outcomes that have already materialized for the patient.

During ongoing patient management in situations requiring vigilance to rapidly ascertain emerging respiratory deterioration, each patient may over a period of time see many doctors and many nurses. Such fragmentation of responsibility for the care process challenges the ability of each provider to quickly and accurately grasp the meaning of the constellation of accumulating clinical and laboratory facts about the patient, to understand trends that may be developing in the patient's health status, and to evaluate the urgency of attention that is necessary to effectively address existing or newly developing issues or to successfully prevent potential adverse events and complications.

Additionally, the qualities of the respiratory sounds of a person who has a chronic respiratory condition may be constantly and profoundly abnormal at all times and yet the person maintains a state of homeostatic compensation of these abnormalities most of the time and only infrequently experiences a disturbance of said state sufficient to exhaust the patient's physiologic compensatory capacity and produce clinically significant deterioration. As such, the conventional technologies and approaches utilized to care for these patients are unable to accommodate the wide range of abnormalities and accurately distinguish deterioration-prone changes from changes that are inconsequential.

Other problems with conventional technologies for respiratory deterioration detection and prediction include that the predictive models typically rely upon measurements that are often performed in an infrequent, imprecise, and inconsistent manner. For example, measurement of pulmonary function ought in principle to be a relatively accurate and precise process. However, ordinary non-quantitative techniques for stethoscopic auscultation and interpretation of breath sounds on the part of the observer are associated with substantial within-observer and between-observer variability. By contrast, variables whose measurements do not present such difficulties (such as quantitative analysis of respiratory sounds acquired by digital devices that can be used by the patient or their in-home caregiver) are amenable to more accurate, precise determinations and, moreover, are amenable to frequent, serial repeated determinations.

Figure 2:
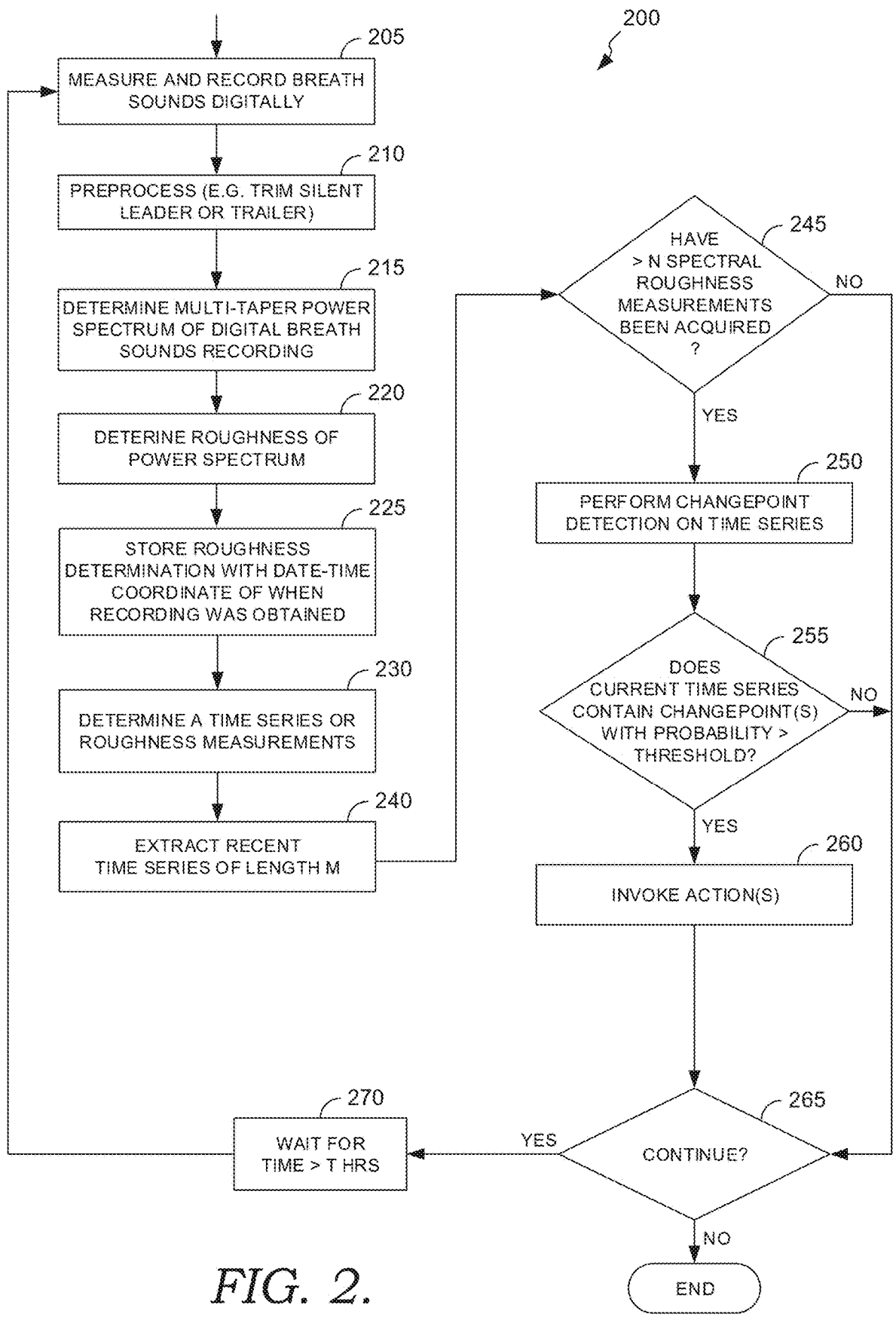
FIG. 2 depicts a flow diagram showing a method utilized by a decision support tool for generating a forecast of likely respiratory deterioration for a patient, and if needed, implementing one or more response actions based on the generated forecast, in accordance with an embodiment of the present disclosure.

Turning now to FIG. 2, a flow diagram is provided that illustrates a method 200 for generating a forecast of likely respiratory deterioration for a patient, and if needed, implementing one or more response actions based on the generated forecast. At a high level, and a described above, embodiments of the technologies described herein may first determine and utilize a time series of spectral roughness, which may be determined using digitized respiration sound information (such as recorded digital audio) from a human patient. From the time series of spectral roughness determinations corresponding to a plurality of respiratory cycles, the presence (or absence) of changepoints may be determined and used to generate a score or forecast indicating respiratory deterioration or likelihood of future deterioration.

Yet another problem with conventional technologies for respiratory deterioration detection and prediction is that the variables that are included in the predictions are often temporally 'lagging indicators' (such as SpO2 or blood gas CO2 or pH levels or other metabolic indicators of respiratory function), which broadly characterize a background of diminished organ-system capacity related to balance of lung ventilation and lung and tissue perfusion factors.

Another significant problem of these technologies, which may be due to the specific variables utilized and their conventional processes for acquiring physiological data, is limited statistical sensitivity and specificity, with substantial false-negative and false-positive rates.

Some conventional technologies for respiratory deterioration detection and prediction measure respiratory sounds by acoustical techniques, but these technologies typically focus on deriving parameters related to the amplitude spectrum of the sound signal, such as the negatively-trending slope of the amplitude spectrum as frequency increases. But this approach also suffers from the statistical sensitivity and specificity problems. In contrast, embodiments described herein provide an improvement to respiratory deterioration detection or prediction technology by determining and utilizing an irregularity of the power-vs-frequency or "roughness" of the power spectrum (or of frequency bands within the power spectrum).

Further still, current technologies must rely on higher quality sound recordings and higher quality conversion of sound recordings into a signal (or data) that is useful for ascertaining indicators that portend deterioration. This is particularly necessary in patients with longstanding respiratory disease who are distinctly abnormal at all times, even when deterioration is not imminent. This sufficient quality requirement of recording sound intensity and converting the sound signal into a signal that is useful or reliable presents another significant problem, especially in a context where a patient may self-administer recording sessions, off-the-shelf consumer electronics (e.g., smartphones) may be used, or the patient may not be in a perfectly controlled environment when the recordings are obtained. Consequently, using these conventional technologies, a patient's respiratory deterioration may go unnoticed, unpredicted, or predicted over a much smaller future time interval.

Embodiments disclosed herein solve these and other problems and thus provide improved diagnostic and predictive decision support technology to facilitate patient care. For example, as described above, these embodiments may identify subtle patterns in respiratory sounds' power spectral roughness properties that presage departures from homeostatic conditions, which can in turn can lead to respiratory failure events or unplanned presentation to acute health care facilities such as emergency departments (EDs). Moreover, some embodiments can accommodate frequent acquisition of digital respiratory sounds recordings, which may be performed by the patient or by an in-home caregiver, and do not require that the sounds measurements be made at precise, periodic intervals, but instead tolerate significant clock or phase jitter in the measured time series. Embodiments presented herein, such as those using power spectra and spectral roughness for diagnosis and intervention, enable the use non-conventional recording respiratory recoding methods that are not routinely utilized or performed by conventional methods. For example, in some embodiments, respiratory sound information may be gathered by electronic or digital stethoscopes, and may even be gathered by consumer grade electronics, such as a smartphone, as previously described. The technology described herein enables the use of these types of electronics, which were not and could not be used by conventional methods, and thus, the use of these electronics is not well-understood, routine, or conventional in the field. By using some of the methods described herein, digital stethoscopes, recorders, smartphones, etc. may now be utilized to gather information that is useful for diagnosis and intervention of some respiratory issues, including respiratory deterioration. In some cases, the transformation of respiratory information from the time domain to the frequency domain may enable these devices to perform higher functions, such as collecting information for diagnostic and intervention purposes, and in some cases, enabling the devices themselves to become diagnostic and interventional tools. As such, the capabilities of these electronic devices is improved, thereby improving the underlying technology, itself.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, a block diagram is provided showing aspects of an example computing system architecture suitable for implementing an embodiment of this disclosure and designated generally as example operating environment 100. Example operating environment 100 provides an aspect of a computerized system for compiling and/or running aspects of this disclosure including monitoring, determining, and/or predicting deterioration of respiratory functioning and decision support technology to facilitate caring for patients who may experience respiratory deterioration.

Operating environment 100 is one example of a suitable environment and system architecture for implementing an embodiment of the disclosure. Other arrangements and elements can be used in addition to or instead of those shown, and some elements may be omitted altogether for the sake of clarity. Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer (i.e., computing device) as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, functions performed by these components, or services carried out by these components may be implemented at appropriate abstraction layer(s) such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example system 200, it is contemplated that in some embodiments functionality of these components can be shared or distributed across other components.

Environment 100 includes one or more electronic health record (EHR) systems, such as EHR system(s) 160 communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, insurance, collections or claims records systems; and may be implemented in or as a part of computer system 120. Similarly, EHR system(s) 160 may perform functions for two or more of types of EHR systems (not shown). EHR system(s) 160 also may include records of urinalysis variables obtained via one or more measurement apparati, tests, or screenings, such as measurement device 141. may perform functions for two or more of types of EHR systems (not shown). In an embodiment, EHR system(s) 160 includes historical claims data for health services, apportionment data, and related health services financial data.

In some embodiments of the technologies described herein, aspects of decision support for patients having or at risk for respiratory deterioration may utilize data about a population of patients derived from patient EHR or other records information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system(s) 160 include one or more data stores of health-related records, which may be stored on storage 121, and may further include one or more computers or servers that facilitate the storing and retrieval of the health records. In some embodiments, EHR system(s) 160 and/or other records systems may be implemented as a cloud-based platform or may be distributed across multiple physical locations. EHR system(s) 160 may further include record systems, which store real-time or near real-time patient (or user) information, such as wearable sensor or monitor, bedside, laboratory, or in-home patient monitors or sensors, for example, such as measurement device 141.

Example operating environment 100 further includes a user/clinician interface 142 and decision support application 140, each communicatively coupled through network 175 to an EHR system 160. Although environment 100 depicts an indirect communicative coupling between interface 142 and application 140 with EHR system 160 through network 175, it is contemplated that an embodiment of interface 142 or application 140 are communicatively coupled to EHR system 160 directly. An embodiment of decision support application 140 comprises a software application or set of applications (which may include programs, routines, functions, or computer-performed services) residing on a client computing device (or distributed in the cloud and on a client computing device) such as a personal computer, laptop, smartphone, tablet, or mobile computing device. In an embodiment, the application is a Web-based application or applet, and may be used to provide or manage user services provided by an embodiment of the technologies described herein, which may be used by a caregiver or screener to provide, for example, information about the likelihood of a specific patient or population of patients to be undergoing deterioration of respiratory functioning or to experience respiratory deterioration at a future time, and may further include a degree or level of deterioration or likely deterioration. In some embodiments, application 140 includes or is incorporated into a computerized decision support tool, as described herein. Further, some embodiments of application 140 utilize user/clinician interface 142.

In some embodiments, application 140 and/or interface 142 facilitates accessing and receiving information from a user or health care provider about a specific patient or set of patients, according to the embodiments presented herein. Embodiments of application 140 also may facilitate accessing and receiving information from a user or health care provider about a specific patient, caregiver, or population including historical data; health care resource data; variables measurements, time series, and predictions (including plotting or displaying the determined outcome and/or issuing an alert) described herein; or other health-related information, and facilitates the display of results, recommendations, or orders, for example. For instance, in an embodiment this information may comprise audio recordings of respiratory cycles; information derived from the audio recordings, such as power spectra, roughness, or time-series data; or information regarding other actions that may be invoked due to a patient's likelihood of experiencing respiratory deterioration, such as notifications, recommendations, care plan changes, or orders. In an embodiment, application 140 also facilitates receiving orders, staffing scheduling, or queries from a user, based on the results of monitoring and/or forecasted outputs, which may in some embodiments utilize user interface 142. Decision-Support application 140 may also be used for providing diagnostic services or evaluation of the performance of various embodiments.

In some embodiments, user/clinician interface 142 may be used with application 140, such as described above. One embodiment of user/clinician interface 142 comprises a user interface that may be used to facilitate access by a user (including a clinician/caregiver such as a medical caregiver, physical therapist, or the like) to a score or prediction determined according to the technologies described herein, including information indicating a likelihood that a patient is experiencing or will experience deterioration of respiratory functioning or other aspects of forecasts for respiratory condition described herein. One embodiment of interface 142 takes the form of a graphical user interface and application, which may be embodied as a software application (e.g., decision support application 140) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, interface 142 includes a Web-based application (which may take the form of an applet or app) or set of applications usable to manage user services provided by an embodiment of the technologies described herein.

In some embodiments, interface 142 may facilitate providing the output of the determined forecast(s), probabilities (or score), recommendations, scheduling orders, providing instructions (such as measuring, recording, and/or otherwise obtaining respiratory information using a digital stethoscope), confirmations or notifications (such as confirmation that information has been received or notifications that information has not been received and there may be an error in the recording device or user operation of the device), reminders (such as notifications to record a respiratory cycle), or outputs of other actions described herein, as well as logging and/or receiving other feedback from the user/caregiver, in some embodiments. In an embodiment, interface 142 also facilitates receiving orders for the patient from the clinician/user, based on the results of monitoring and predictions. Interface 142 also may be used for providing diagnostic services or evaluation of the performance of various embodiments.

Example operating environment 100 includes measurement device 141 communicatively coupled through network 175 to an EHR system 160. The term measurement is used broadly herein, and it is contemplated that in some embodiments, measurement device 141 may not perform measurement but may receive information about physiological parameters (such as respiratory variables) which may be measured, observed, or otherwise recorded. Embodiments of measurement device 141 may comprise one or more sensors, such as sensor(s), an interface component, and/or processing/communications component (not shown). In some embodiments, measurement device 141 may comprise a BT stethoscope wirelessly communicatively coupled with an application on a computing device, such as a smartphone running an app. For example, in one embodiment actually reduced to practice and described below, measurement device 141 comprises an Eko Devices Inc. Eko Core1® digital stethoscope or a Thinklabs Inc. Thinklabs One® digital stethoscope and may be configured to acquire 30-second audio recordings and transmit the digital audio files from the stethoscope via BlueTooth radio to a nearby cellphone (which may operate as computer system 120 or carry out some or all of the process performed by computer system 120 described herein) for communication to EHR(s) 160. In some embodiments, measurement device 141 may be capable of recording audio of patient breathing over frequencies sufficient to encompass the features of crackles, ronchi, stridor, and other non-vesicular, abnormal respiratory sounds.

Embodiments of measurement device 141 may store user-derived data locally or communicate data over network 175 to be stored remotely. Some embodiments of measurement device 141 include a monitor interface, which may be embodied as I/O such as buttons and sounds emitted from the measurement device 141, its firmware or software application or app operating on a user's mobile device or computer system 120, and in an embodiment may facilitate uploading of measured (or recorded, or otherwise received) information from measurement device 141 to computer system 120.

Additionally, some embodiments of measurement device 141 include functionality for processing user-derived information locally or for communicating the information to computer system 120, where it is processed. In some embodiments, the processing may be carried out or facilitated by one or more software agents, as described below. In some embodiments the processing functionality, performed on measurement device 141 and/or computer system 120 includes pre-processing and/or signal conditioning, such as removing noise or erroneous information.

Example operating environment 100 further includes computer system 120, which may take the form of one or more servers, and which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, aspects of application 140 or interface 142 may operate on or utilize computer system 120. Similarly, a portion of computing system 120 may be embodied on user interface 142, application 140, and/or EHR system(s) 160. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local services or may be distributed across one or more components of operating environment 100, in the cloud, on one or more personal computers or servers such as system 120, and/or a computing device running interface 142 or application 140. In some embodiments, interface 142 and/or application 140 operate in conjunction with software stack 125.

In embodiments, model variables indexing (or mapping) service 122 facilitate retrieving patient physiological variables, which may include frequent item sets, extracting database records, and/or cleaning the values of variables in records. For example, service 122 may perform functions for synonymic discovery, indexing or mapping variables in records, or mapping disparate health systems' ontologies, such as determining that a particular medication frequency of a first record system is the same as another record system. Predictive models service 124 comprises computing services or routines for forecasting likelihood of respiratory deterioration, which may be developed and implemented according to the method described in connection to FIG. 2. In some embodiments, services 122 and 124 may invoke computation services 126.

Computation services 126 may perform statistical or computing operations, and may include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages such as packages psd, for performing power spectral density estimates; tuneR, for performing audio analysis and extraction of audio features; signal, for performing signal processing functions including sampling/resampling, filtering and visualization functions; nlme, for performing modeling, fitting, comparing or related functions of linear and nonlinear mixed effects models; rpart, for performing recursive partitioning for classification, regression and survival trees; spatstat, for performing spatial point pattern analysis, model-fitting, simulation, spatial sampling, or related testing; grid, for graphics related operations; and bcp, for performing change-point detection or analysis.

Computation services 126 also may include natural language processing services (not shown) such as Discern nCode™ developed by Cerner Corporation, or similar services. In an embodiment, computation services 126 include the services or routines, which may be embodied as one or more software agents or computer software routines such as the example embodiments of computer program routines illustratively provided in FIGS. 6A-8. Computation services 126 also may include services or routines for utilizing one or more prediction models such as described in connection to FIG. 2 and the example computer program routines illustratively provided in FIGS. 6A-8. In some embodiments, computation services 126 use EHR system(s) 160, model data and model storage services (not shown), and/or other components of example operating environment 100, and may also include services to facilitate receiving and/or pre-processing physiological data. For instance, model data and model storage services may be utilized to perform services for facilitating storage, retrieval, and implementation of the forecasting models described herein and of the data used in the models.

Some embodiments of stack 125 may further comprise services for utilizing an Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) 128. For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
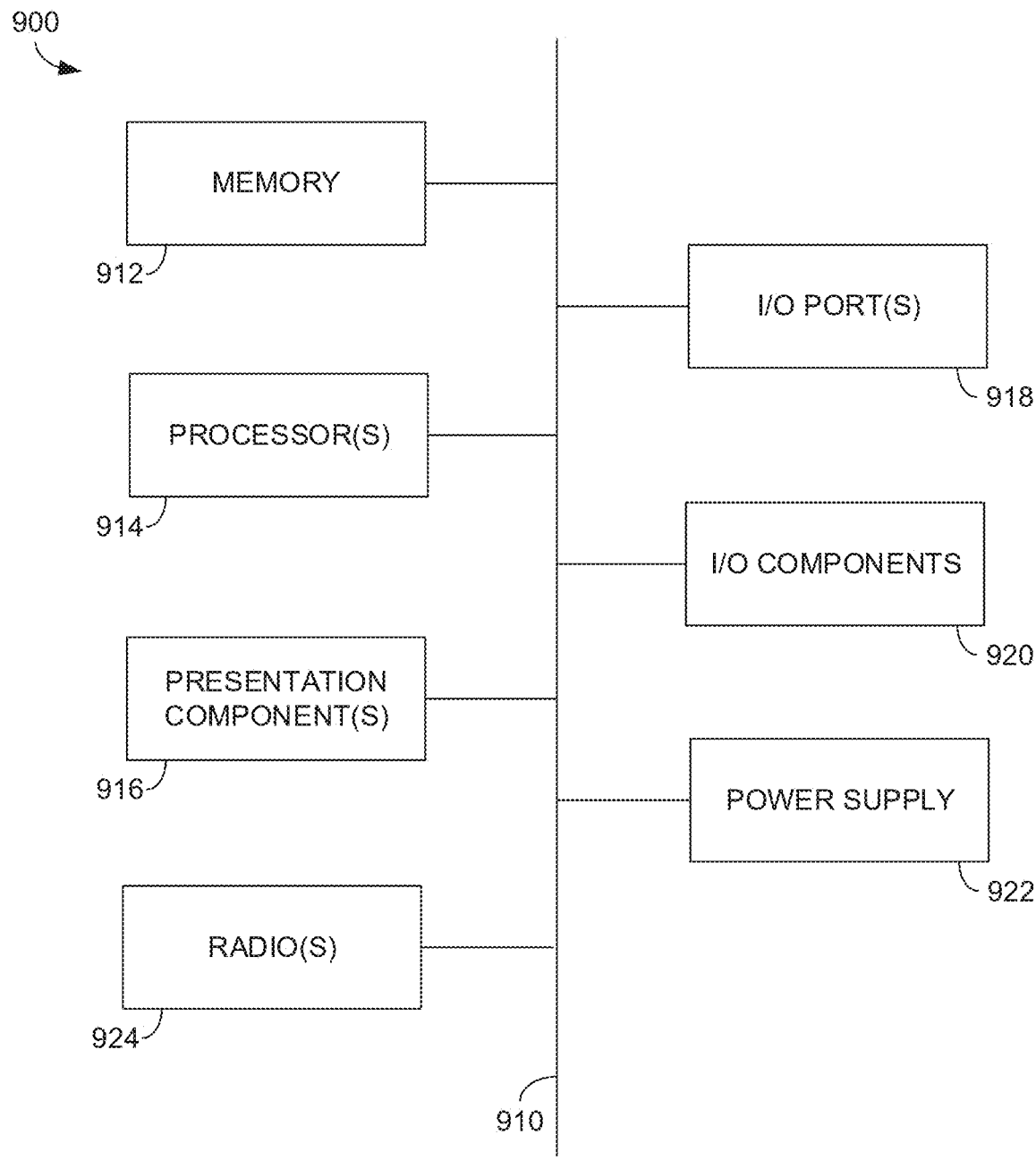

Turning briefly to FIG. 1B, there is shown one example embodiment of computing system 900 representative of a system architecture that is suitable for computer systems such as computer system 120. Computing device 900 includes a bus 910 that directly or indirectly couples the following devices: memory 912, one or more processors 914, one or more presentation components 916, input/output (I/O) ports 918, input/output components 920, radio 924, and an illustrative power supply 922. Bus 910 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an example computing system architectures that can be used in connection with one or more embodiments of the present disclosure. Distinction is not made between such categories as "workstation," "server," "laptop," "hand-held device," etc., as all are contemplated within the scope of FIG. 1B and reference to "computing system."

Computing system 900 typically includes a variety of computer-readable media. Computer-readable media can be any available media that can be accessed by computing system 900 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 900. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above may be included within the scope of computer-readable media.

Memory 912 includes computer-storage media in the form of volatile and/or nonvolatile memory. The memory may be removable, non-removable, or a combination thereof. Exemplary hardware devices include solid-state memory, hard drives, optical-disc drives, etc. Computing system 900 includes one or more processors that read data from various entities such as memory 912 or I/O components 920. Presentation component(s) 916 present data indications to a user or other device. Exemplary presentation components include a display device, speaker, printing component, vibrating component, etc.

In some embodiments, computing system 924 comprises radio(s) 924 that facilitates communication with a wireless-telecommunications network. Illustrative wireless telecommunications technologies include CDMA, GPRS, TDMA, GSM, LTE, WiMAX, and the like. Radio 924 may additionally or alternatively facilitate other types of wireless communications including Wi-Fi, Bluetooth, NFC, other types of RF communication, light, infrared, or the like. As can be appreciated, in various embodiments, radio 924 can be configured to support multiple technologies and/or multiple radios can be utilized to support multiple technologies.

I/O ports 918 allow computing system 900 to be logically coupled to other devices, including I/O components 920, some of which may be built in. Illustrative components include a microphone, joystick, game pad, satellite dish, scanner, printer, wireless device, etc. The I/O components 920 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 900. The computing system 900 may be equipped with depth cameras, such as stereoscopic camera systems, infrared camera systems, RGB camera systems, touchscreen technology, and combinations of these, for gesture detection and recognition. Additionally, the computing system 900 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Turning now to FIG. 2A, a flow diagram is provided that illustrates a method 200 for generating a forecast of likely respiratory deterioration for a patient, and if needed, implementing one or more response actions based on the generated forecast. At a high level, and a described above, embodiments of the technologies described herein may first determine and utilize a time series of spectral roughness, which may be determined using digitized respiration sound information (such as recorded digital audio) from a human patient. From the time series of spectral roughness determinations corresponding to a plurality of respiratory cycles, the presence (or absence) of changepoints may be determined and used to generate a score or forecast indicating respiratory deterioration or likelihood of future deterioration.

With reference to FIG. 2, roughness or total curvature is often defined as the integral of the squared second derivative or as the Hausdorff Dimension of the function. Some embodiments described herein, including example method 200, transform raw digital respiratory sound recordings into power spectra, which are two-dimensional functions of acoustic power to frequency, and then determine roughness of the power spectrum. In particular, the inventor has determined a process that utilizes the roughness of the amplitude of the power spectrum of respiratory sounds as a function of frequency for a measure of emergent deterioration of respiratory function, and the embodiments described herein establish that this roughness may be utilized as a reliable, early measure of emergent deterioration. In particular, the shape of the power spectrum is highly variable between patients and even within any one patient over time. The quantitative amplitude of peaks in the power spectrum is also variable within each patient over time. However, the degree of spectral roughness is typically quite stable when the patient is in a state of homeostatic compensation. Intervals of emerging decompensation or deterioration are characterized by increased spectral roughness, with higher-amplitude features in various frequency bands appearing and disappearing over a period of approximately 6 to 72 hours. Further, while there does not appear to be a consistent pattern in terms of which features are evoked at which frequencies; some embodiments actually reduced to practice have shown that there is an overall effect of increased spectral roughness, particularly in the band between 600 Hz and 1.5 KHz.

Accordingly, at step 205, information comprising breathing sounds of a target patient are acquired. The breathing sounds may be acquired (or otherwise received) as digital audio recordings. In particular, in embodiments of step 205, the breathing sounds may be measured and/or recorded, such as by using a digital stethoscope as described herein, or this information representing or derived from recent but already measured and recorded breathing sounds may be received. The information may be received from a patient record associated with the patient such as a record in an EHR, such as EHR(s) 160, or a measurement device 141, which may include receiving the information from a memory buffer associated with the measurement device. In some embodiments of step 205, a measurement device 141, such as a digital stethoscope may be bound or associated with a particular target patient's EHR or an account associated with the patient, such that serial measurements for the target patient may be more easily obtained the measurement device 141.

In some embodiments of step 205, the bandwidth of the microphone sensor and stethoscope apparatus (or similar measurement device 141 used for recording breathing sounds) are sufficient to encompass the frequencies of the crackles, ronchi, stridor, and other non-vesicular, abnormal respiratory sounds that may not only characterize worsening of respiratory function but also may characterize aspects of the state of comparative respiratory homeostasis of a person having chronic respiratory disease in their routine, stable condition when not in danger of imminent respiratory deterioration. In some embodiments, the length of each digital stethoscopic recording of respiratory sounds is sufficient so as to characterize the predominant respiratory status of the patient. For instance, in one example embodiment actually reduced to practice, a recording of 8 or more respiratory cycles (which may equate to a recording lasting approximately 30 seconds in length for an ambulatory adult) is sufficient.

Figure 3A:
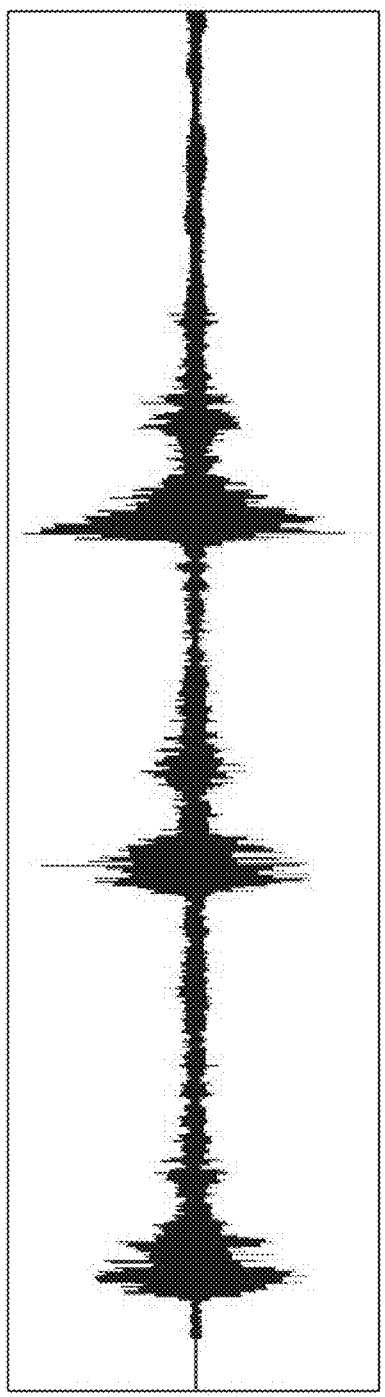
FIGS. 3A-3E depict examples of audio waveforms (digital sound recordings) of respiratory cycles for patients including healthy and respiratory events and indications of deterioration, for use in an example embodiment actually reduced to practice.
Figure 3B:
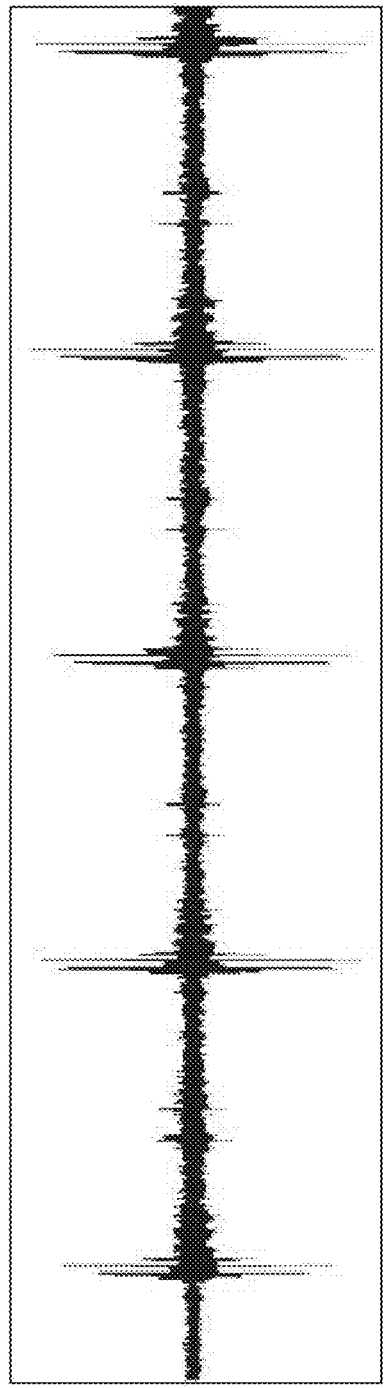
Figure 3C:
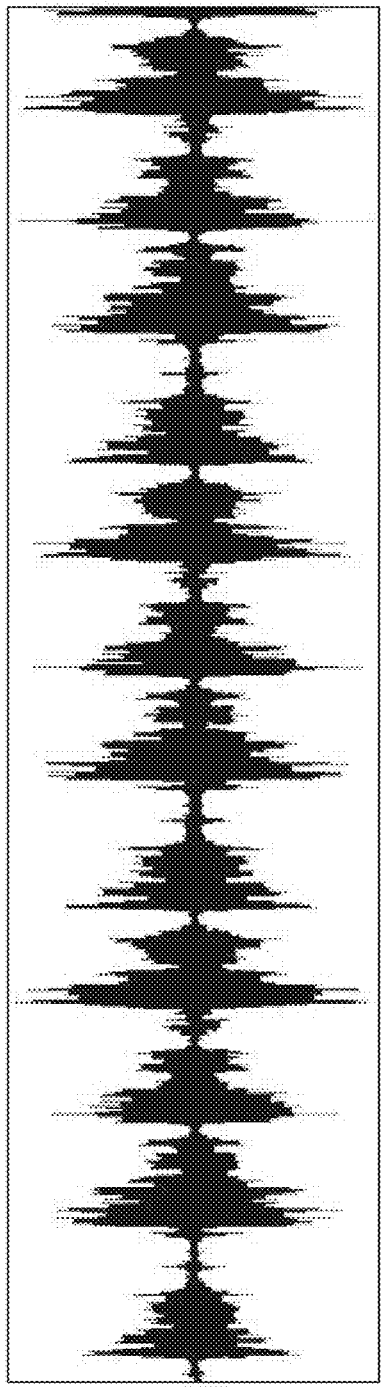
Figure 3D:
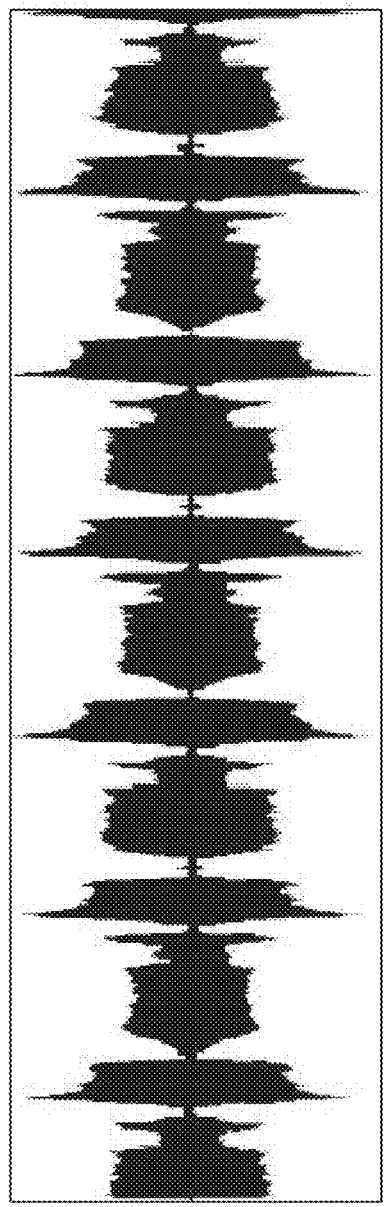
Figure 3E:
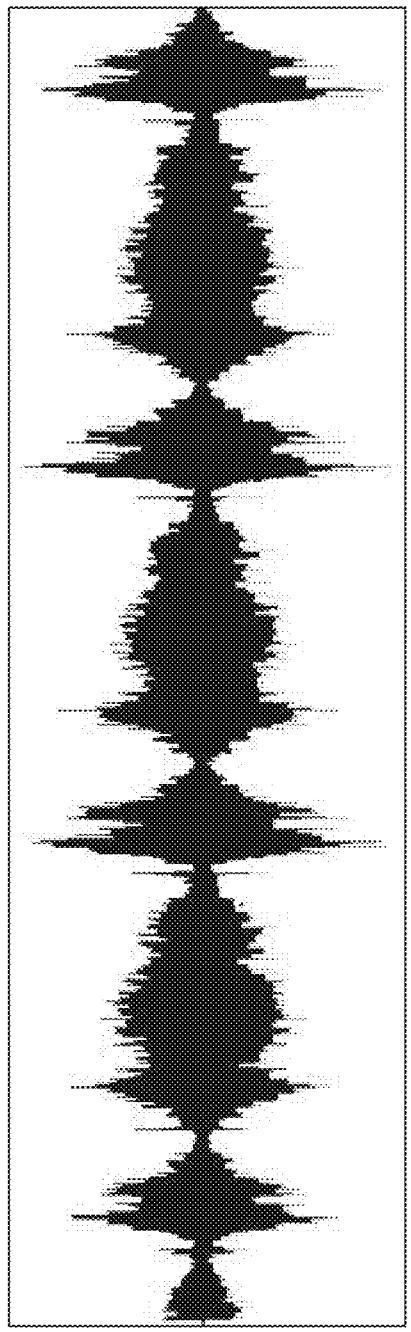
Figure 4A:
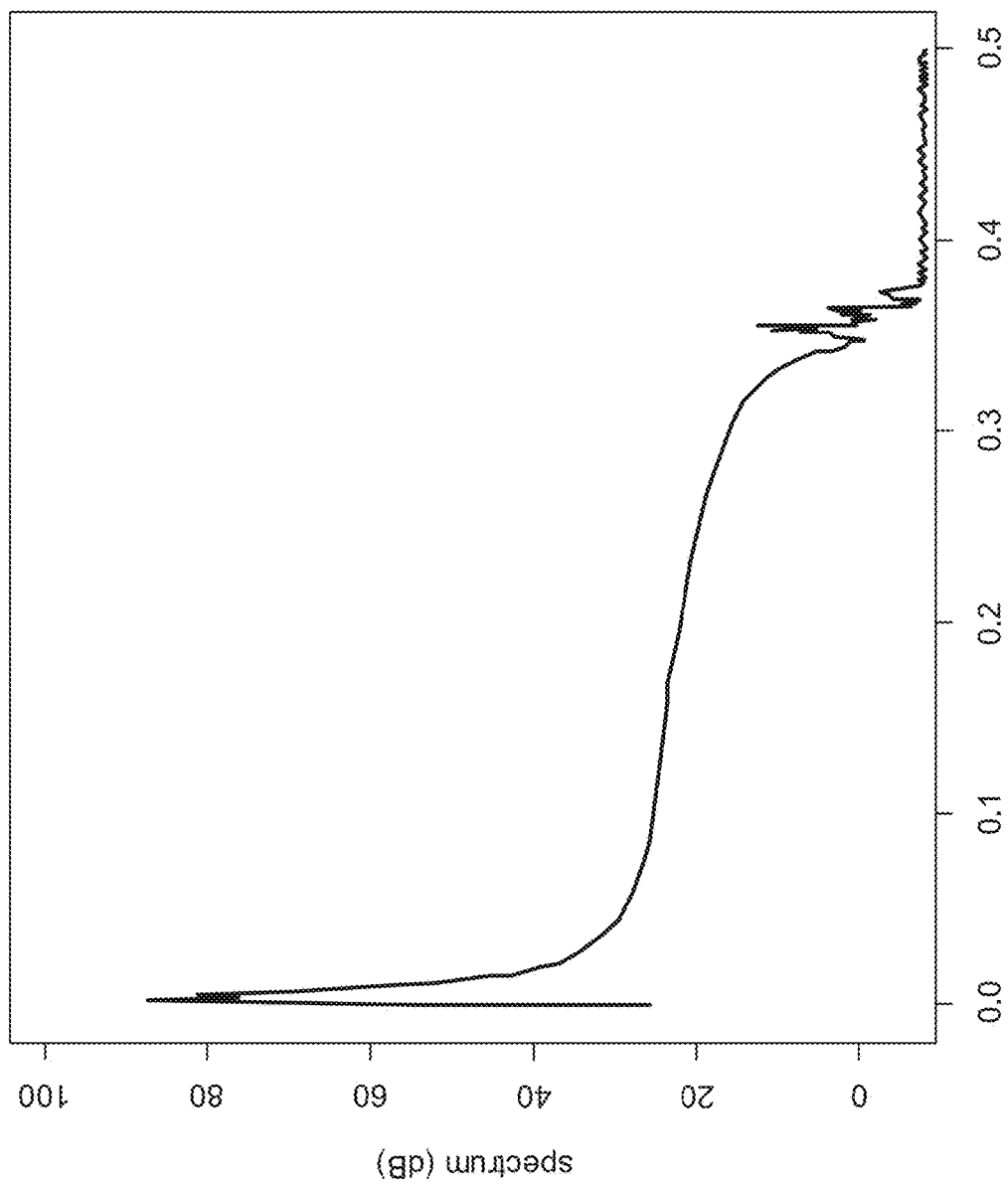
FIGS. 4A-4E depict representations of the respiratory sound power spectra determined from the example recordings of FIGS. 3A-3E.
Figure 4B:
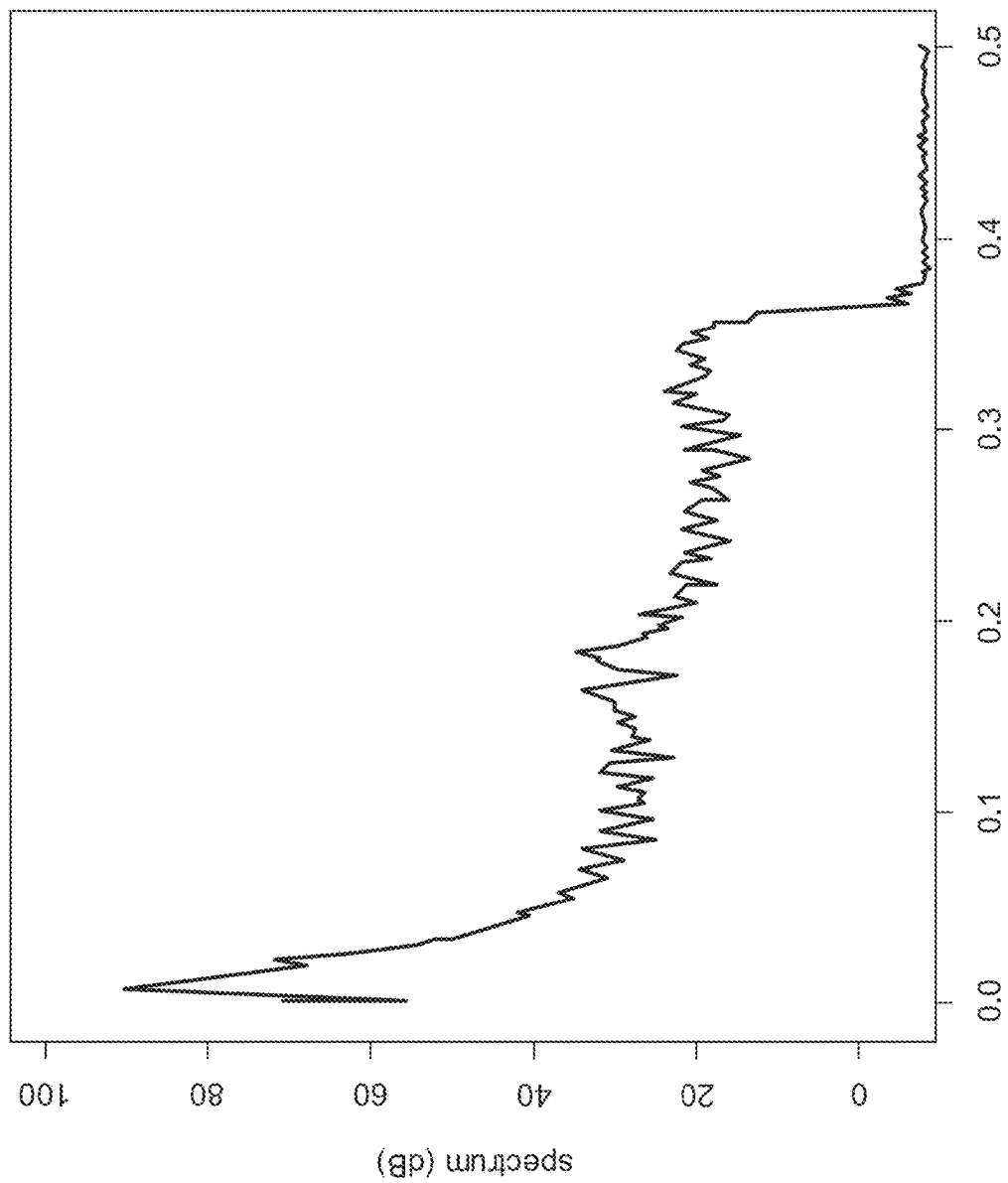
Figure 4C:
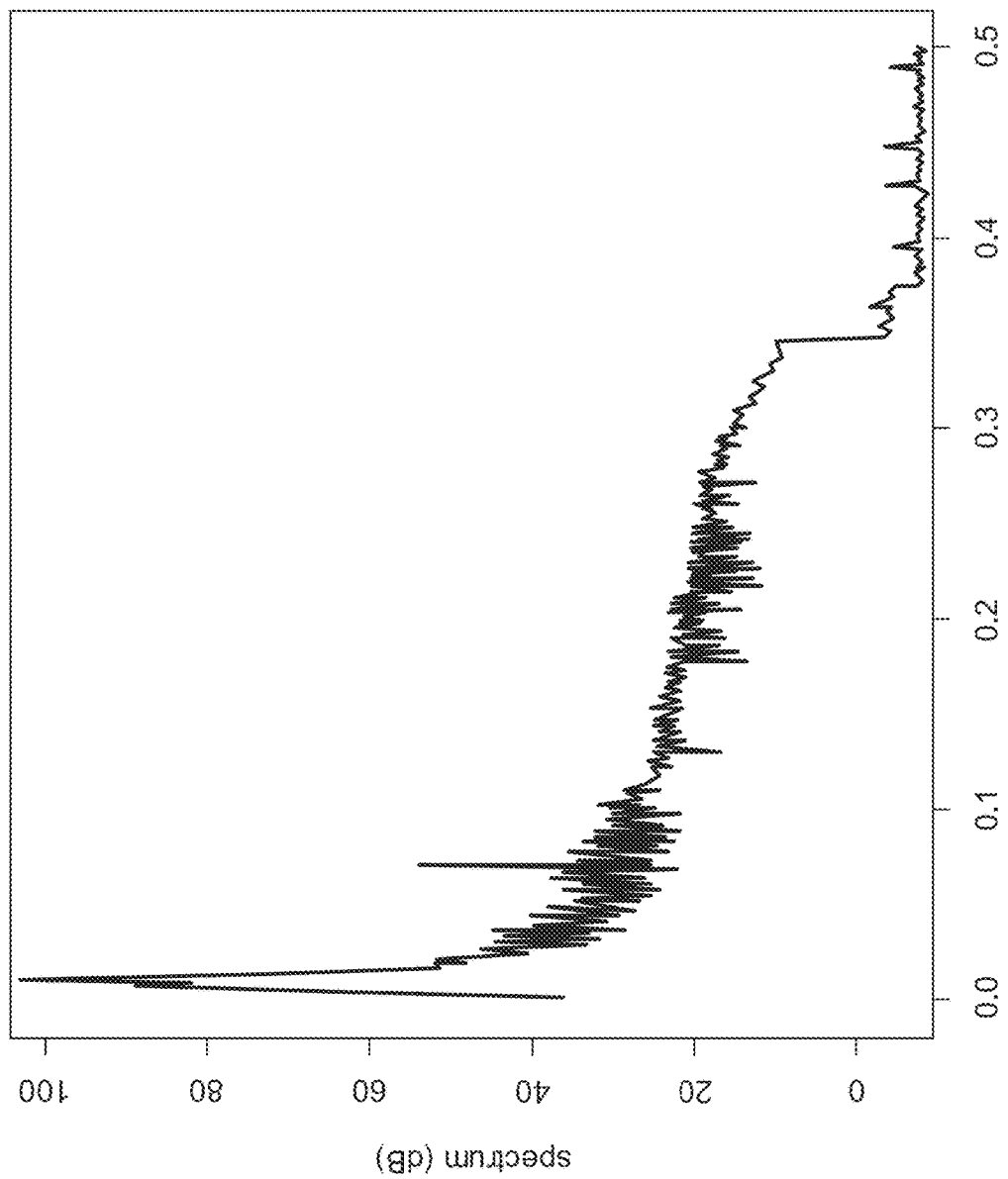
Figure 4D:
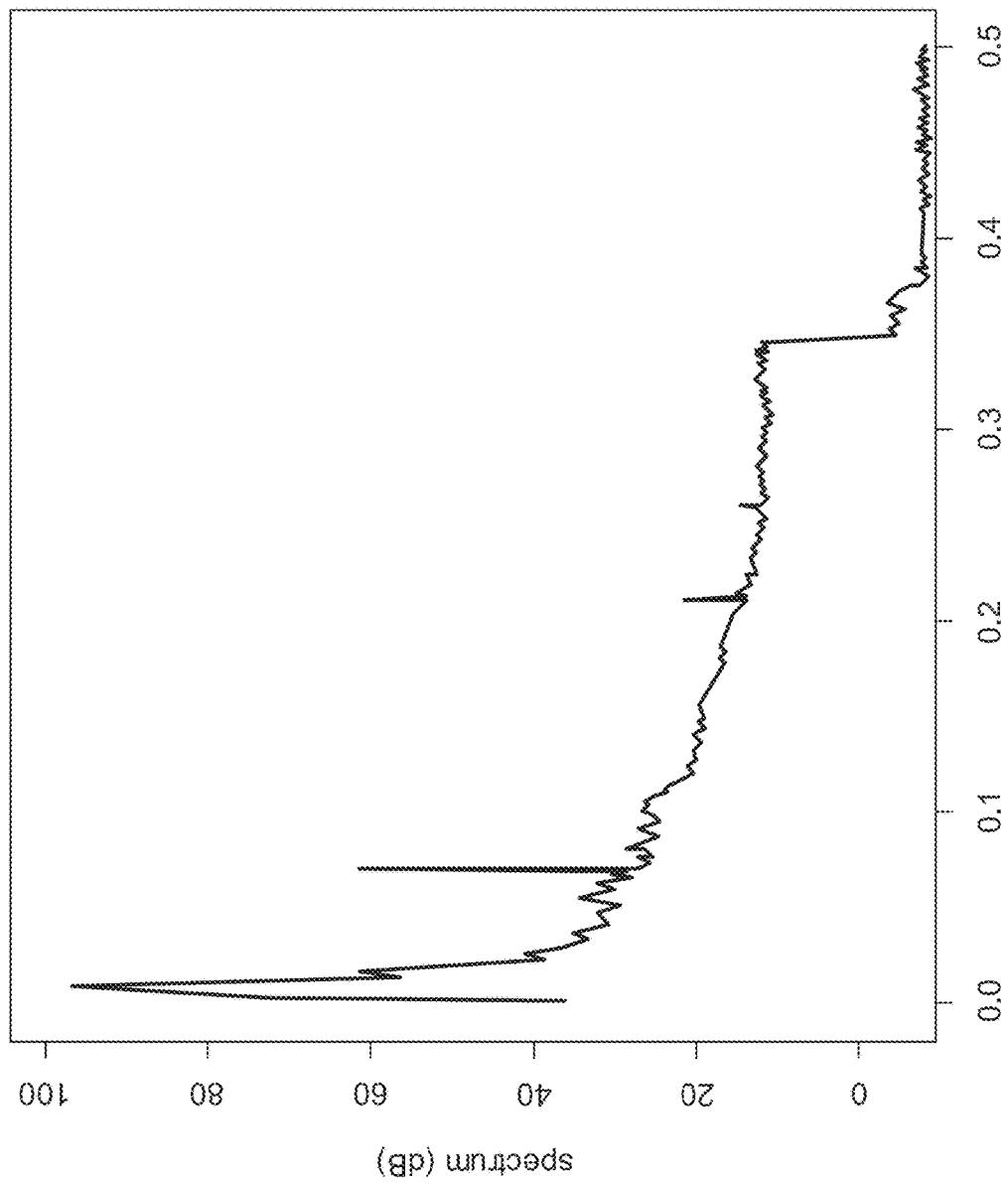
Figure 4E:
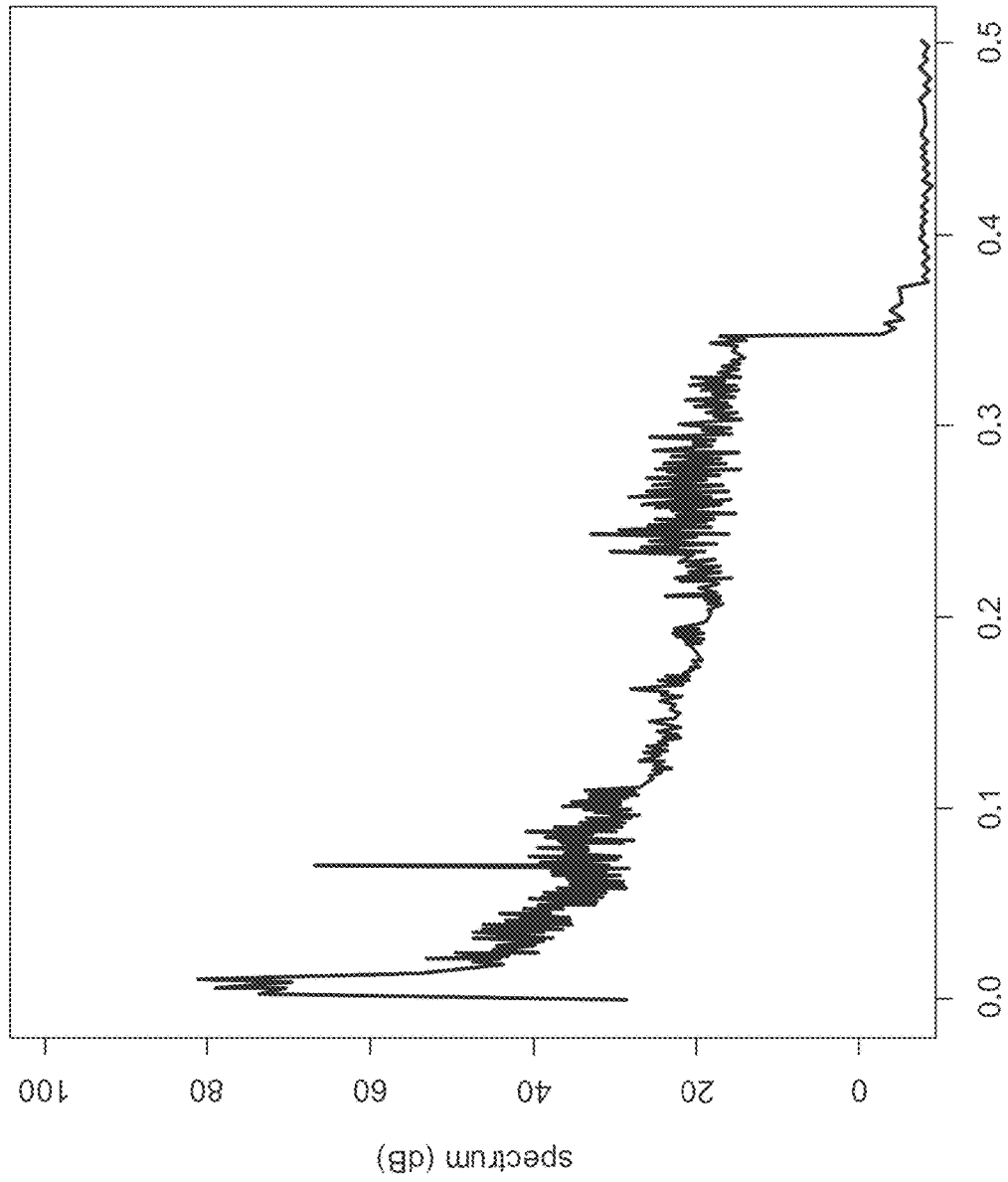

Example waveforms illustratively depicting the information acquired or received in step 205 are shown in FIGS. 3A-3E. In particular, with reference to these drawings, example waveforms of digital audio information for patients having various respiratory features in their breathing including healthy normal breathing (FIG. 3A), crackles (FIG. 3B), ronchi (FIG. 3C), and stridor (FIG. 3D). FIG. 3E depicts an example waveform of a digital audio recording of a COPD patient with emerging deterioration.

At step 210, preprocessing, such as described herein, may be performed on the digital audio information representing breathing sounds of the target patient. For example, preprocessing may include trimming silent leaders or trailers of recorded audio (e.g., audio that does not capture a patient's respiratory cycles, such as audio that may be recorded while the patient is manipulating the stethoscope to prepare for recording). Similarly, preprocessing may comprise processing the audio to remove anomalous events or measurements (e.g., sneezing or speaking), normalizing, pre-whitening, or spectral whitening, equalizing or filtering the audio recording, or otherwise processing it to prepare the digital information for one or more subsequent steps of method 200.

At step 215, the power spectra of the digital recording of breath sounds is determined. Embodiments of step 215 may determine a multi-taper power spectrum of each digital recording of breath sounds. In particular, the digital waveform of audio samples determined from step 205 may be utilized for computing the power spectra. In some embodiments, determining the power spectrum from recorded digital waveform information may be performed by Fourier Transform or Wavelet Transform. Some embodiments of step 215 (and other steps of method 200) utilize computation services 126 (FIG. 1), including, in one example embodiment actually reduced to practice and further described below, R System packages psd, tuneR, and/or signal. One example embodiment of step 215 is provided in FIGS. 6A-6C, which depict an example computer program routine for generating a multi-taper power spectrum of digitized respiratory sound information. FIGS. 4A-4E depict example graphical representations of power spectra determined from the example waveforms of respiratory cycles described in connection with FIGS. 3A-3E.

At step 220, roughness of the power spectra are determined. In particular, a roughness of the power spectrum determined in step 220 for each respiratory cycle is determined. In some embodiments, spectral roughness may be determined by using the integral of second derivative or Hausdorff Dimension. In some embodiments, more than one of these or suitable processes may be utilized to determine roughness, and more than one time series assembled (one time series corresponding to each process used to determine roughness). (In these embodiments, steps 230 through 255 may be carried out for each roughness time series. In particular, with regard to step 255, if a changepoint probability exceeds a threshold for any of the time series, an action may be invoked.)

Continuing, with step 220, embodiments of step 220 may utilize computation services 126 (FIG. 1), including, in one example embodiment, R System packages nlme, rpart, and/or spatstat. An example embodiment of step 220 is shown in FIGS. 7A-7B, which provides an example computer program routine for determining roughness of a power spectrum in band 0.1 to 0.3 dimensionless frequency as integral of second derivative and as Hausdorff Dimension of spectrum log amplitude. This example further shows determining the roughness from the power spectral of the example respiratory cycles described in connection to FIGS. 3A-3E. In some embodiments, multiple At step 225, the roughness determined in step 220 may be stored and associated with the date/time information for when the respiratory information was obtained. In this way, a time series of roughness determinations can be determined in step 230. In some embodiments, the time series comprises at least N roughness determinations. N may be as little as one measurement, but more measurements, over a recent time interval on the order of days-to-weeks or a month, may yield better results.

At step 240 the time series may be pruned to include only the most recent entries. In some embodiments, the time series is pruned to length M where M corresponds to the last five to ten measurements. In other embodiments, M may be three or less or 30 or more, however, M must be sufficient so as to perform changepoint determination in step 250. At step 245, some embodiments of method 200 confirm that the time series comprises at least N roughness determinations. If this is not so, then method 200 proceeds to step 265 and may continue to acquire respiratory information that can be used to derive new roughness determinations for the time series. If there are sufficient roughness determinations in the time series, then method 200 proceeds to step 250.

At step 250, changepoint detection is performed on the time series. In some embodiments, univariate changepoint analysis may be performed on the measures of spectral roughness either by Bayesian methods or by frequentist methods, such as are known to those skilled in the art of statistical process control and signal analysis. In an example embodiment reduced to practice described below, a Bayesian Markov Chain Monte Carlo (MCMC) method was employed, with a burn-in of 1,000 iterations and MCMC run of 5,000 iterations.

At step 255, the changepoint determination is evaluated against a threshold. In particular, if a probability of one or more potential changepoint(s) exceeds the threshold, then a changepoint event is determined (or detected). In this way, transgressing the probability threshold is an assertion of a changepoint event. In one embodiment, the threshold is 0.5 or more than fifty percent likely that a changepoint event has occurred.

If at step 255, a changepoint event is not determined to have occurred (i.e., the probability threshold is not exceeded), then method 200 proceeds to step 265. If a changepoint event is detected, then at step 260, one or more actions may be invoked as described previously. For example, the decision support tool may emit an alert to a caregiver via a decision support application 140, display a warning on a graphical user interface (such as user/clinician interface 142), generate a recommendation regarding the patient's disposition or care, or other action as described herein. In an embodiment, the decision support tool further determines whether the patient requires intensified monitoring or intervention, or may provide specific recommendations of care or may automatically schedule intervention by caregivers, consultations by specific caregivers, other healthcare resources (such as diagnostics or orders), or additional or modified care. In some embodiments, an application and graphical user interface are provided for displaying information related to the one or more actions and/or displaying aspects of the patient's condition based on the resulting determinations provided from method 200.

At step 265, method 200 may continue or end. In some embodiments, method 200 continues so that more respiratory cycle information (and ultimately more spectral roughness measurements) may be determined. In some embodiments, method 200 may repeat continuously, periodically, occasionally, as needed, or when new respiratory information data becomes available.

At step 270, if method 200 continues, then a time interval may lapse before repeating the method so that the next iteration of method 200 collects and determines new information because the patient's condition has changed. In some embodiments, step 270 may wait 36 hours before proceeding back to step 205 and repeating method 200.

EXAMPLE REDUCTION TO PRACTICE

With reference now to FIGS. 5-8 and continuing reference to FIGS. 1A and 2, an example embodiment actually reduced to practice is described. This example reduced to practice used a server cluster (computer system 120) running the Linux operating system (operating system 129), the open-source statistical software package R, and the R modules psd, tuneR, signal, nlme, rpart, spatstat, grid, and bcp.

A set of de-identified, secondary-use-consented, EHR-derived, HIPAA-compliant digital stethoscope recordings from 12 human patients whose care episodes had previously been completed and for whom the respiratory outcomes were already known was extracted from a commercially-available electronic health record system (Cerner Health Millennium® EHR). Digital stethoscopes, including Eko Devices Inc. Eko Core1® and Thinklabs Inc. Thinklabs One® were utilized for acquiring 30-sec recordings and transmitting the digital audio files from the stethoscope via BlueTooth radio to a nearby cellphone, and thereafter transmitted by cellphone to the EHR via Cerner CareAware iBus™ connection.

Figure 5:
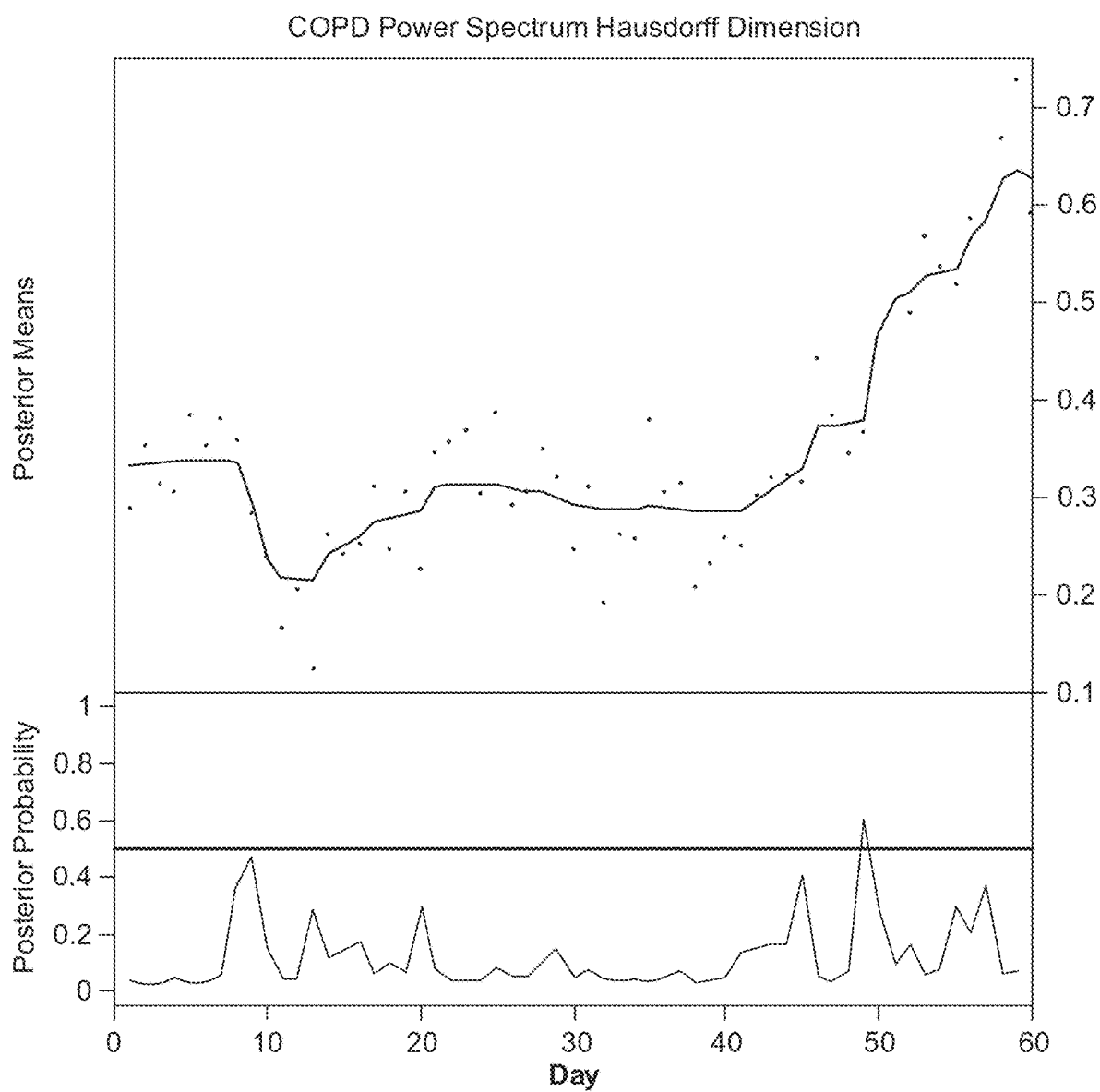
FIG. 5 depicts an example time series of Hausdorff Dimension values of a COPD patient who was admitted to hospital on Day-59 subsequent to detection of a changepoint at Day-49, based on an example embodiment actually reduced to practice.

In this example embodiment, preprocessing was performed on the digitized respiratory data using a computer program (illustratively provided in FIGS. 6A-6C) developed using the R open source system and modules to trim leading and trailing segments from each of the respiratory sound recordings. Multi-taper power spectra were then calculated from the trimmed MP3 digital audio files. The Hausdorff Dimension and integral of the spectra second-derivatives were determined as indices of spectral roughness. (FIGS. 7A and 7B illustratively provide an example computer program depicting this.) Bayesian changepoint determinations from power spectrum roughness time-series were computed for each of the subjects. (FIG. 8 illustratively provides an example computer program utilized for this.) Both Hausdorff Dimension and integral of second-derivative measures yielded identical results for changepoints in the patients' time series examined. Optionally and in some embodiments, a representative power spectrum of a patient can be used as a "baseline" reference for calculation of differential Hausdorff Dimension values involving subsequent power spectra compared to the patient's own "baseline" spectrum. FIG. 5 depicts an example time series of Hausdorff Dimension values of a COPD patient who was admitted to hospital on Day-59 subsequent to detection of a changepoint at Day-49. In particular, the in the upper portion of FIG. 5, the solid line represents the central tendency of the Bayesian estimates a posterior of the most recent measurement. The lower portion shows Bayesian measure of probability that a person would have had either an unplanned emergency department visit or admission to a hospital. At approximately day 49, the probability threshold (represented by the line, which is at fifty percent or 0.5) is transgressed, indicating a changepoint event. In some embodiments, at this point an alert would be emitted or other action invoked. Accordingly, embodiments improve upon the prior respiratory monitoring technologies by providing advanced warning—in this example a ten day warning—to intervene and save the patient and/or reduce likelihood of hospital admission.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention. Some example embodiments include the following:

Embodiment 1: A decision support tool for monitoring or treating a human patient prone to respiratory deterioration, the decision support tool comprising: a computer processor; computer memory storing computer-readable instructions that when executed by the computer processor perform operations comprising: receiving respiratory information comprising a plurality of recorded measurements of respiratory cycles for the patient; determining a power spectra for the respiratory information; determining spectral roughness of the determined power spectra; determining a time series of spectral roughness determinations, each element in the time series having a time corresponding to the time of the plurality of recorded respiratory cycles; performing a changepoint analysis on the time series to determine a changepoint event; and in response to determining a changepoint event, determining to initiate an intervening action.

Embodiment 2: Embodiment 1, wherein the respiratory cycles are determined using a digital stethoscope and the recorded measurements of respiratory cycles comprise digitized audio information of the patient breathing.

Embodiment 3: Any of Embodiments 1-2, wherein the respiratory cycles comprise at least eight cycles.

Embodiment 4: Any of Embodiments 1-3, wherein the spectral roughness is determined by integral of second derivative or Hausdorff Dimension.

Embodiment 5: Any of Embodiments 1-4, wherein a changepoint event is determined based on exceeding a predetermined probability threshold.

Embodiment 6: Any of Embodiments 1-5, wherein the threshold is 0.5.

Embodiment 7: Any of Embodiments 1-6, wherein the intervening action comprises issuing an alert.

Embodiment 8: A method for determining a changepoint signal from a time series of spectral roughness of digital respiration sound signals representing respiration, the method comprising: associating a recording digital stethoscopic sensor with a human patient such that recordings made with said sensor will be registered as belonging to said patient; repeatedly placing at least one microphone sensor in contact with thoracic skin of a human patient for a time interval sufficient to record a plurality of respiratory cycles of the patient and the respiratory sounds emitted thereby; acquiring a plurality of digital recordings of breath sounds over serial time intervals, each said interval comprising multiple inspiration-expiration cycles of the patient; detecting respiration sounds' signal onset and offset in each such recording and distinguishing said respiration sounds from background noise; comparing an intensity of said sound signal to a threshold to determine whether said sound signal intensity in each time interval is sufficiently strong with respect to background noise so as to provide a representative sampling of sounds associated with airflow in the patient's respiratory tract; digitally recording said digital respiration sound signals and storing said signals on machine-readable media for subsequent computer analysis; loading previously-stored pneumophonography digital respiration sound signals into computer memory for processing; trimming leader and trailer portions from the digital sound signals; determining a multi-taper power spectrum of each trimmed digital respiratory sound signal; measuring the amplitude variability or roughness of each said power spectrum within a passband of frequencies; storing said roughness measurement(s) with the date-time coordinate denoting when the recording associated with the power spectrum was obtained; retrieving and assembling roughness measurements time series and performing changepoint detection on said spectral roughness time series; if the probability of said changepoint(s) exceeds threshold, asserting that one or more likely changepoint events has been detected; and electronically notifying a caregiver and/or the patient of said assertions of detected changepoint(s) meriting decisions and action so as to prevent deterioration of respiratory function or minimize the severity or risk associated with deterioration that is not preventable.

Embodiment 9: Embodiment 8, wherein said cycles comprise at least 8 breaths, and said detecting of respiration sound signal onset and offset and said distinguishing of said respiration sounds from background noise comprises: firstly determining from said sound signal intervals in which signal intensity is below a threshold denoting either absence of respiratory activity or non-contact of the stethoscope with the thoracic skin in the region of lung fields; and secondly where said sound signal intensity rises above said threshold at a beginning of inspiration; thirdly where said sound signal intensity rises above said threshold at a beginning of expiration; fourthly where an effective respiratory rate is determined from a plurality of said sound signal intervals and the estimated respiratory rate is between 4 and 40 breaths per minute; fifthly where low signal intensity ('silent') or high signal intensity (excessively 'noisy') segments preceding or following said sound signal intervals denoting consecutive respiratory cycles are trimmed from the balance of the recorded sound signal (trimming or censoring of 'leader' and 'trailer' recording segments); sixthly where intervals of the recorded sound signal not meeting said criteria are excluded from subsequent analysis.

Embodiment 10: Any of Embodiments 8-9, wherein said digital stethoscopic recording is digitized at 44.1 KHz per recording channel.

Embodiment 11: Any of Embodiments 8-10, wherein said digital stethoscopic recording has frequency response whose amplitude is flat within 6 dB between at least 100 Hz and 1.5 KHz and more preferably between at least 60 Hz and 6.0 KHz.

Embodiment 12: Any of Embodiments 8-11, wherein said digital stethoscopic recording storage is in a machine-readable form, such as the MP3 format.

Embodiment 13: Any of Embodiments 8-12, wherein said step of determining multi-taper power spectra produces a normalized dimensionless frequency scale from 0.0 to 0.5, where the maximum at 0.5 corresponds to the Nyquist sampling frequency (0.5 times the sampling rate, e.g., 0.5*44.1 KHz=22.05 KHz)

Embodiment 14: Any of Embodiments 8-13, wherein determinations of amplitude variability or spectrum roughness as a function of frequency is by calculating the integral of the second derivative of the power spectrum or by calculating the Hausdorff Dimension of the power spectrum.

Embodiment 15: Any of Embodiments 8-14, wherein said step of determining spectral roughness is within a passband preferably between 600 and 6.0 KHz (equivalent to 0.03 to 0.3 on the normalized dimensionless frequency scale for a 44.1 KHz sampling rate).

Embodiment 16: Any of Embodiments 8-15, wherein said determination of the presence or absence of one or more likely changepoints and the probability thereof within a time series of said spectral roughness values is performed by Bayesian methods for generating samples from the posterior distribution of values over potential changepoint locations and retrospective segmentation or causal predictive filtering, by support vector machine computations, or by other frequentist statistical methods as are known to those practiced in the art.

Embodiment 17: Any of Embodiments 8-16, wherein said probability threshold for said changepoint assertion is preferably at least 0.50.

Embodiment 18: Any of Embodiments 8-17, wherein said step of electronically notifying individuals of detected likely changepoint(s) is via electronic messaging in an electronic health records system, via radiofrequency mobile telecommunications device such as a smartphone or tablet computer, or via electronic mail or other online messaging.

Embodiment 19: An apparatus for non-invasive monitoring of respiration comprising: at least one microphone for obtaining a sound signal from a person, said sound signal representing respiration; an analog-to-digital conversion means for converting said analog microphone signal(s) to digital form for electronic transmission and storage in machine-readable format; means for detecting respiration sounds of sufficient intensity and quality in said digital respiratory sound recordings to be suitable for subsequent determinations of acoustic power spectrum of the sounds and spectral roughness; means for transforming said sound signal to a multi-taper power spectrum; means for determining spectral roughness of said power spectrum; means for generating time series of successive values of said spectral roughness; means for determining the presence or absence of one or more changepoints in said spectral roughness time series; and electronic communication means for providing alerts or interpretive advice to human users or caregivers regarding changes detected in said time series of respiration signal spectral roughness values.

Embodiment 20: Embodiment 19, further comprising an alarm means, such as the decision support module of an electronic health record software system, for processing said spectral roughness of respiration signals and generating an alarm signal when one or more changepoints in said spectral roughness of respiration signal has characteristics representing a condition meriting medical attention.

Embodiment 21: Any of Embodiments 19-20, wherein a representative power spectrum of a patient can be used as a "baseline" reference for calculation of pairwise differential Hausdorff Dimension values involving subsequent power spectra compared to the patient's own "baseline" spectrum.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A decision support tool for monitoring or treating respiratory deterioration, comprising:
   a computer processor;
   computer memory storing non-transitory computer-readable instructions that when executed by the computer processor perform operations comprising:
   receiving respiratory information comprising a plurality of recorded measurements of respiratory cycles, each recorded measurement of a respiratory cycle associated with a time, wherein the respiratory information received was collected using a digital stethoscope;
   determining a power spectra for the respiratory information by transforming the respiratory information into a frequency domain;
   determining spectral roughness of the determined power spectra, the spectral roughness determined for each recorded measurement of the plurality of recorded measurements of respiratory cycles;
   based on the spectral roughness determined for each recorded measurement, determining a time series of spectral roughness determinations;
   performing a changepoint analysis on the time series to determine a changepoint event; and
   in response to determining a changepoint event, automatically initiating an intervening action.

2. The decision support tool of claim 1, further comprising trimming the plurality of recorded measurements to exclude audio not indicative of a respiratory cycle prior to determining the power spectra for the respiratory information.

3. The decision support tool of claim 1, wherein the respiratory information is transformed into the frequency domain using Fourier Transform or Wavelet Transform.

4. The decision support tool of claim 1, wherein the spectral roughness is determined by Hausdorff Dimension.

5. The decision support tool of claim 1, wherein the spectral roughness is determined within a passband between 600 Hz and 6.0 KHz.

6. The decision support tool of claim 1, wherein the changepoint event is determined based on time series of spectral roughness determination exceeding a predetermined probability threshold.

7. The decision support tool of claim 6, wherein the threshold is at least 0.5.

8. The decision support tool of claim 6, wherein the intervening action comprises issuing a notification.

9. One or more non-transitory computer storage media having computer-executable instructions embodied thereon that, when executed, by one or more processors, cause the one or more processors to perform a method for monitoring or treating respiratory deterioration, the method comprising:
   receiving respiratory information comprising a plurality of recorded measurements of respiratory cycles, each recorded measurement of a respiratory cycle associated with a time;
   determining a power spectra for the respiratory information;
   determining spectral roughness of the determined power spectra;
   determining a time series of spectral roughness determinations;
   performing a changepoint analysis on the time series to determine a changepoint event; and
   in response to determining a changepoint event, automatically initiating an intervening action.

10. The media of claim 9, wherein the respiratory information received was collected using at least one of a digital stethoscope, and a smartphone.

11. The media of claim 9, wherein the spectral roughness is determined for a set of recorded measurements pruned from the plurality of recorded measurements of respiratory cycles.

12. The media of claim 9, wherein the spectral roughness is determined by Hausdorff Dimension.

13. The media of claim 9, wherein the changepoint event is determined based on time series of spectral roughness determination exceeding a predetermined probability threshold.

14. The media of claim 9, wherein the intervening action is one of modifying a care program, scheduling an appointment, and generating a notification.

15. A computer-implemented method for monitoring or treating respiratory deterioration, the method comprising:
- receiving respiratory information comprising a plurality of recorded measurements of respiratory cycles, each recorded measurement of a respiratory cycle associated with a time;
- determining a power spectra for the respiratory information;
- determining a time series of spectral roughness determinations, each of the spectral roughness determinations of the time series determined from the power spectra;
- from the time series of spectral roughness, determining a changepoint event; and
- automatically initiating an intervention action in response to the changepoint event.

16. The method of claim 15, wherein the power spectra is determined using Fourier Transform or Wavelet Transform.

17. The method of claim 15, wherein the respiratory information received was collected using at least one of a digital stethoscope and a smartphone.

18. The method of claim 15, wherein the spectral roughness is determined by Hausdorff Dimension.

19. The method of claim 15, wherein the changepoint event is determined based on time series of spectral roughness determination exceeding a predetermined probability threshold.

20. The method of claim 15, wherein the intervening action is one of modifying a care program, scheduling an appointment, and generating a notification.

* * * * *

UNITED STATES PATENT AND TRADEMARK OFFICE
CERTIFICATE OF CORRECTION

| | |
|---|---|
| PATENT NO. | : 11,278,246 B1 |
| APPLICATION NO. | : 16/125467 |
| DATED | : March 22, 2022 |
| INVENTOR(S) | : Douglas S. McNair |

It is certified that error appears in the above-identified patent and that said Letters Patent is hereby corrected as shown below:

In the Drawings

• Sheet 3 of 18 (Reference Numeral 220) (FIG. 2.), and on the title page, the illustrative figure, Line 1: delete "DETERINE" and insert -- DETERMINE--.
• Sheet 5 of 18 (FIG. 3C.), Line 1: delete "RONCHI" and insert -- RHONCHI --.
• Sheet 9 of 18 (FIG. 4C.), Line 1: delete "RONCHI" and insert -- RHONCHI --.
• Sheet 17 of 18 (FIG. 7B.), Line 30: delete "ronchi" and insert -- rhonchi --.

In the Specification

• Column 6, Line 38-51: delete "Turning now to FIG. 2, a flow diagram is provided that illustrates a method 200 for generating a forecast of likely respiratory deterioration for a patient, and if needed, implementing one or more response actions based on the generated forecast. At a high level, and a described above, embodiments of the technologies described herein may first determine and utilize a time series of spectral roughness, which may be determined using digitized respiration sound information (such as recorded digital audio) from a human patient. From the time series of spectral roughness determinations corresponding to a plurality of respiratory cycles, the presence (or absence) of changepoints may be determined and used to generate a score or forecast indicating respiratory deterioration or likelihood of future deterioration." and insert -- One correlate of relatively infrequent assessment of respiratory status of a patient — often in family medicine or pulmonology clinics at intervals of 6 months or more, when combined with the all-too-common fragmentation of the care process with responsibilities divided among dozens of provider personnel most of whom do not have deep or longstanding familiarity with the patient — is that unexpected deterioration of respiratory function occurs to many patients, such that a medical crisis ensues. In many such instances, the impending deterioration could have been discerned or predicted: provided that more frequent respiratory monitoring were acquired in advance; provided that that data were analyzed so as to determine quantitative indicia that are leading indicators of impending respiratory deterioration; and provided that the output of the analytical system and method were effectively communicated to the providers who have the responsibility to intervene and prevent or manage the determined risk of respiratory deterioration. --.

Signed and Sealed this
Eleventh Day of October, 2022

*Katherine Kelly Vidal*
Katherine Kelly Vidal
*Director of the United States Patent and Trademark Office*

CERTIFICATE OF CORRECTION (continued)
U.S. Pat. No. 11,278,246 B1

- Column 12, Line 31: delete "ronchi," and insert -- rhonchi, --.
- Column 14, Line 19: delete "Healthe Intent®." and insert -- HealtheIntent®. --.
- Column 16, Line 39: delete "FIG. 2A," and insert -- FIG. 2, --.
- Column 17, Line 39: delete "ronchi," and insert -- rhonchi, --.
- Column 17, Line 59: delete "ronchi," and insert -- rhonchi, --.
- Column 22, Line 50: delete "KHz)" and insert -- KHz). --.
- Column 22, Line 67: delete "segmenation" and insert -- segmentation --.